(12) United States Patent
Chen et al.

(10) Patent No.: US 10,519,487 B2
(45) Date of Patent: Dec. 31, 2019

(54) KIT AND A METHOD FOR DETERMINING THE PRESENCE OR AMOUNT OF A TARGET NUCLEIC ACID SEQUENCE IN A SAMPLE

(71) Applicant: City University of Hong Kong, Kowloon (HK)

(72) Inventors: Ting-Hsuan Chen, Kowloon Tong (HK); Zichen Zhao, Kowloon Tong (HK); Shan Chen, Kowloon Tong (HK); Ka I Au Ieong, Kowloon Tong (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 15/239,926

(22) Filed: Aug. 18, 2016

(65) Prior Publication Data

US 2018/0051324 A1 Feb. 22, 2018

(51) Int. Cl.
*C12Q 1/6827* (2018.01)

(52) U.S. Cl.
CPC .................................. *C12Q 1/6827* (2013.01)

(58) Field of Classification Search
CPC ..... C12Q 1/6823; C12N 15/1013; C12M 1/00
See application file for complete search history.

(56) References Cited

U.S. PATENT DOCUMENTS

| | | | |
|---|---|---|---|
| 8,975,017 B2 | 3/2015 | Gumbrecht et al. | |
| 8,980,561 B1 | 3/2015 | Cai et al. | |
| 9,091,631 B2 | 7/2015 | Petruno et al. | |
| 2004/0009506 A1* | 1/2004 | Stephan | C12Q 1/682 506/9 |

OTHER PUBLICATIONS

Chen1 et al, AuNPs Amplified Magnetophoretic Effect for Colorimetric Detection of Nucleic Acid, 2015, Proceedings of the 10th IEEE International Conference on Nano/Micro Engineered and Molecular Systems (IEEE-NEMS 2015) Xi'an, China, published on Apr. 7-11, 2015. (Year: 2015).*
Chen2 et al, Enzyme-Free Amplification by Nano Sticky Balls for Visual Detection of ssDNA/RNA Oligonucleotides, 2015, Appl. Mater. Interfaces, 7, 22821-22830 (Year: 2015).*
Thomson et al, Amplification free detection of Herpes Simplex Virus DNA, 2011, Analyst, 136, 1599-1607. (Year: 2011).*
Zhao et al, Visual detection of nucleic acids based on Mie scattering and the magnetophoretic effect, 2015, Analyst, 140, 7876-7885 (Year: 2015).*
Data sheet-1a Sequence alignment between P1rpoB probe and pagA probe using BLAST Global Alignment program, printed on Feb. 5, 2019 pp. 1-2 (Year: 2019).*
Data sheet-2a Sequence alignment between P2rpoB probe and pagA probe using BLAST Global Alignment program, printed on Feb. 5, 2019 pp. 1-2 (Year: 2019).*
Data sheet-3a Sequence alignment between HSVp2 probe and CMV probe using BLAST Global Alignment program, printed on Feb. 5, 2019 pp. 1-2 (Year: 2019).*
Data sheet-4a Sequence alignment between HSVp2 probe and CMV probe using BLAST Global Alignment program, printed on Feb. 5, 2019 pp. 1-2 (Year: 2019).*

\* cited by examiner

*Primary Examiner* — Narayan K Bhat
(74) *Attorney, Agent, or Firm* — Renner Kenner Greive Bobak Taylor & Weber

(57) ABSTRACT

A method for determining the presence or amount of a target nucleic acid sequence in a sample, uses magnetic particles loaded with a probe and polystyrene particles loaded with a probe, in particular a different probe, for directly or indirectly detecting the presence or amount of the target nucleic acid sequence which is in particular indicative of a disease. The methods of the present invention allow for determining target nucleic acid sequences even in low abundance and in complex samples with advantageous sensitivity and, thus, represent promising approaches which can in particular be used in the diagnosis of several diseases and health conditions. A kit comprising a loaded magnetic particle and a loaded polystyrene particle is provided and can be used for the methods of the present invention, in particular for diagnosis or prognosis of a disease in a subject such as a human.

11 Claims, 20 Drawing Sheets

Specification includes a Sequence Listing.

KIT AND A METHOD FOR DETERMINING THE PRESENCE OR AMOUNT OF A TARGET NUCLEIC ACID SEQUENCE IN A SAMPLE

SEQUENCE LISTING

The Sequence Listing file entitled "SequenceListing" having a size of 4,757 bytes and creation date of 18 Aug. 2016 that was electronically filed with the patent application is incorporated herein by reference in its entirety.

TECHNICAL FIELD

The present invention relates to methods for determining the presence or amount of a target nucleic acid sequence in a sample, in particular based on a magnetophoretic assay. The present invention also pertains to a kit comprising a magnetic particle and a polystyrene particle and is suitable for a magnetophoretic assay for determining the presence or amount of a target nucleic acid sequence.

BACKGROUND OF THE INVENTION

Short, single-stranded nucleic acids often serve as important factors for determining a disease or bioterrorism agent. The detection of these nucleic acids has broad applications, such as in pathogen identification and disease diagnosis. Many platforms have been developed for detecting nucleic acid molecules with specific sequences, including polymerase chain reaction (PCR), bio-barcode-based detection and electrochemistry. PCR-based methods, in particular, have been largely used to detect nucleic acids in ultralow abundance. However, this approach requires labor-intensive procedures and cumbersome instrumentation. These limitations have created significant challenges in healthcare medication in developing countries and other resource-limited sites. For example, one of reasons of the Ebola virus outbreak in Africa was the lack of diagnostic facilities in their local hospitals and clinics. Thus, effective detection and diagnosis, suitable for low-resource settings, is of particular importance.

In recent years, the development of visual detection methods based on gold nanoparticles (AuNPs), silver nanoparticles and graphene oxide has increased rapidly because of their simplicity and the visual readouts produced. Numerous methods based on AuNP aggregation have been developed to detect DNAs/RNAs, proteins and metal ions. To improve its sensitivity, enzymatic or non-enzymatic DNA circuits were further employed. An AuNP-based assay using magnetic microparticles (MMPs) was developed as a magnetophoretic assay with a significantly reduced detection time and a simplified equipment requirement. However, although AuNPs are widely used, their modification is time-consuming and requires delicate protocols to stabilize their mono-dispersion. For example, the mono-dispersed AuNPs are sensitive to the ionic strength of the solution. Alteration of the ionic strength may result in undesirable aggregation, creating additional uncertainty in optimizing the assay sensitivity and repeatability and making it incompatible with complex environments such as bio-fluids. On the other hand, the intrinsic colour of a biological sample can create significant interference for colorimetric assays. Consequently, delicate preparation or biomarker purification may be required, which restricts the practicality of the assay.

In addition, the current bottleneck of visual detection sensitivity usually falls at a nanomoles per liter level and is insufficient for detecting target molecules in low abundance. Various amplification methods have been developed, e.g. enzymatic amplification. However, enzymatic amplifications require specific conditions for enzymatic reactions, e.g., thermal cycles, and special storage for protein enzymes that may be difficult for resource-limited sites. Biobarcode amplification uses target molecules to connect nanoparticles that carry a vast number of barcode DNAs. The barcode DNAs, whose amount is proportional to the target molecules, are subsequently dissociated from the nanoparticles and detected, resulting in amplified signals representing the target molecules. However, the dissociation of biobarcode DNAs requires time-consuming dithiothreitol (DTT) treatment or toxic cyanides, which may increase complexity of the assays.

Accordingly, there remains a strong need for methods for determining the presence or amount of target nucleic acid sequences indicative of a health condition or a disease of an individual for subsequent diagnosis or prognosis based on a simple procedure, with low instrumentation requirements and sufficient sensitivity. In particular rapid and time-saving approaches are urgently required for specifically detecting the presence or amount of viral nucleic acid sequences and/or disease-indicative sequences in an individual so as to allow for an early diagnosis and early treatment of the individual. The present invention therefore provides novel approaches for such a purpose.

SUMMARY OF THE INVENTION

The present invention relates to methods for determining the presence or amount of a target nucleic acid sequence in a sample, in which methods magnetic particles loaded with a probe and polystyrene particles loaded with a probe, in particular a different probe, are used for directly or indirectly detecting the presence or amount of the target nucleic acid sequence which is in particular indicative of a disease.

The present invention relates in a first aspect to a method for determining the presence or amount of a target nucleic acid sequence in a sample comprising steps of:

(a) adding a magnetic particle loaded with a first probe and a polystyrene particle loaded with a second probe to the sample and applying conditions such that the target nucleic acid sequence in the sample binds to the loaded magnetic particle and to the loaded polystyrene particle to form a complex comprising the target nucleic acid sequence bound to the loaded magnetic particle and to the loaded polystyrene particle;

(b) applying a magnetic force to separate the complex from the mixture of step (a);

(c) determining at least one of a physical feature of the mixture after separating the complex in step (b) or the amount of the complex separated in step (b).

In particular, the first probe and the second probe are single strand nucleic acid sequences linked to biotin which can bind to a biotin-binding compound coated on the magnetic particle and on the polystyrene particle. The physical feature as determined in step (c) is preferably at least one of the colour, turbidity or spectral absorbance of the mixture. The presence or the corresponding amount of the target nucleic acid sequence can be determined based on the physical feature or based on the amount of the complex separated in step (b).

In a second aspect, the present invention pertains to a method for determining the presence or amount of a target nucleic acid sequence in a sample comprising steps of:

(a) adding a first magnetic particle loaded with a first probe and a gold particle loaded with a second probe to the sample and applying conditions such that the target nucleic acid sequence in the sample binds to the first loaded magnetic particle and to the loaded gold particle to form a first complex comprising the target nucleic acid sequence bound to the first loaded magnetic particle and to the loaded gold particle;

(b) applying a magnetic force to separate the first complex from the mixture of step (a);

(c) separating the loaded gold particle from the first complex separated in step (b);

(d) adding a second magnetic particle loaded with a third probe and a polystyrene particle loaded with a fourth probe to the loaded gold particle of step c) and applying conditions such that the second probe of the loaded gold particle binds to the second loaded magnetic particle and to the loaded polystyrene particle to form a second complex comprising the second probe of the loaded gold particle bound to the second loaded magnetic particle and to the loaded polystyrene particle; and (e) applying a magnetic force to separate the second complex from the mixture of step (d);

(f) determining at least one of a physical feature of the mixture after separating the second complex in step (e) or the amount of the second complex separated in step (e).

In particular, the first, third and fourth probes are single strand nucleic acid sequences linked to biotin and the second probe is a single strand nucleic acid sequence linked to a thiol group. The biotin in the probes binds to a biotin-binding compound comprised in the coating of the magnetic particle and of the polystyrene particle. The second probe on the gold particle is preferably a single strand nucleic acid sequence linked to a polyethylene glycol (PEG) and a thiol group at the 3' end. The separation in step (c) is preferably carried out by heating.

The present invention also provides a kit comprising a magnetic particle loaded with a probe and a polystyrene particle loaded with a probe. In particular, the probe on the magnetic particle and the probe on the polystyrene particle are different and are preferably a single strand nucleic acid sequence each linked to biotin. The kit may additionally include a gold particle loaded with a probe.

Further, the present invention also relates to a device suitable for use in determining the presence or amount of the target nucleic acid sequence in the methods described above. The device includes an inlet port and a micro-channel, wherein the micro-channel has a neck portion with a diameter smaller than the size of the loaded polystyrene particle. In particular, the device includes an inlet port, a mixing zone, a first collection zone subjected to a magnetic field, a second collection zone with a micro-channel, a capillary pump and a reservoir. The micro-channel is preferably marked with indicia for direct measurement of the amount of the loaded polystyrene particle being trapped in the micro-channel.

Accordingly, the present invention provides novel and highly advantageous methods for detecting a target nucleic acid sequence which are especially suitable for further diagnosis and prognosis of a disease or a health condition of a subject. Without intending to be limited by theory, it has been found that the methods as described above are highly sensitive for detecting target nucleic acid sequences even in low abundance. The methods are, thus, exceptionally suitable for their detection and measurement in a multiplex sample mixture such as blood and serum.

In particular, the application of polystyrene particles in the present invention provides an exceptional stability against interfering biomolecules in the sample. Providing the polystyrene particles in a micro-scale range further allows an easy detection of changes, i.e. through colour, turbidity or spectral absorbance changes. Accordingly, the present invention provides an advantageous method for an easy, fast and reliable visual determination of a target nucleic acid sequence even in complex samples and even if it is present in low abundance in the sample.

BRIEF DESCRIPTION OF THE DRAWINGS

FIG. 3A shows optical images showing the changes in solution turbidity in response to different concentrations of $T_{rpoB}$, namely from 0M to 50 nM of $T_{rpoB}$. FIG. 3B shows UV-Vis spectral absorbance of the suspension of those in FIG. 3A. FIG. 3C shows the relative UV-Vis spectral absorbance at 400 nm of the suspension from repeated experiments (mean±SEM, n=3). FIG. 3D shows analysis of the relative UV-Vis spectral absorbance at 400 nm of the suspension resulting from varying concentrations of $T_{rpoB}$. Inset: the linear range between the concentration of $T_{rpoB}$ and the relative UV-Vis spectral absorbance at 400 nm. The absorbance of the suspension resulting from the blank sample (hybridization buffer with 0 M target nucleic acid sequence) was used as the reference.

FIG. 4A shows optical images showing the changes in solution turbidity in response to the concentrations of $T_{rpoB}$, namely from 0M to 128 μM of $T_{rpoB}$. FIG. 4B shows UV-Vis spectral absorbance of the suspension of those in FIG. 4A. FIG. 4C shows the relative UV-Vis spectral absorbance at 400 nm of the suspensions from repeated experiments (mean±SEM, n=3). FIG. 4D shows the analysis of the relative UV-Vis spectral absorbance at 400 nm of the suspension resulting from varying concentrations of $T_{rpoB}$. Inset: the linear range between the concentration of $T_{rpoB}$ and the relative UV-Vis spectral absorbance at 400 nm. The absorbance of the suspension resulting from the blank sample (hybridization buffer with 0M target nucleic acid sequence) was used as the reference.

FIG. 7A shows optical images and relative UV-Vis spectral absorbance at 400 nm showing the changes of solution turbidity when $T_{rpoB}$ was present at 100 pM or absent in the nucleic acid pool. The absorbance resulting from the blank sample (solution of nucleic acid pool without target nucleic acid sequence) was used as the reference. The relative absorbance is derived from repeated experiments (mean±SEM, n=3). FIG. 7B shows optical images and relative UV-Vis spectral absorbance at 400 nm showing the changes in solution turbidity with varying concentrations of $T_{rpoB}$, namely from 1M to 50 nM. The absorbance of the suspension resulting from the blank sample (hybridization buffer with 0 M target nucleic acid sequence) was used as the reference. The relative absorbance is derived from repeated experiments (mean±SEM, n=3).

FIG. 13A shows optical images showing the change of solution turbidity resulting from ssDNA MB155. FIG. 13B shows the spectral absorbance of the solution with PMP suspension resulting from ssDNA MB155. FIG. 13C shows the relative absorbance at 400 nm of data shown in FIG. 13B (mean±max deviation, n=3). Absorbance of the solution with PMP suspension resulting from the control sample was used as the reference. FIG. 13D shows the linear range of the relative absorbance with respect to the concentration of ssDNA MB155. FIG. 13E shows the spectral absorbance of the solution with PMP suspension resulting from ssRNA MBr155. FIG. 13F shows the linear range of the relative absorbance with respect to the concentration of ssRNA MBr155 (mean±max deviation, n=2).

FIG. 14A shows optical images and relative absorbance at 400 nm of the solution with PMP suspension resulting from the control sample, solutions containing SNP A, SNP T, or SNP C with single-base-mismatched sequence, or solution containing MB155 with complementary sequence (mean±max deviation, n=3). Absorbance of the solution with PMP suspension resulting from the control sample was used as the reference. FIG. 14B shows the spectral absorbance of the solution with PMP suspension.

FIG. 15A shows optical images and relative absorbance at 400 nm of solution with PMP suspension resulting from the control sample or solutions containing target oligonucleotides MB 155 with varying concentrations (0 M, 10 pM, 50 pM, 100 pM, 250 pM in 45 μL) (mean±max deviation, n=4). Absorbance of the solution with PMP suspension resulting from the control sample was used as the reference. FIG. 15B shows the spectral absorbance of the solution with PMP suspension.

FIG. 16A shows a qRT-PCR analysis of the relative expression of miR-155 from MDA cells or MCF cells (mean±SEM, n=3). FIG. 16B shows optical images and relative absorbance at 400 nm of the solution with PMP suspension resulting from the control sample or solutions containing extracted microRNAs (mean±max deviation, n=3). FIG. 16C shows the spectral absorbance of the solution with PMP suspension. FIGS. 16D and 16E show the relative absorbance at 400 nm of the solution with PMP suspension resulting from microRNAs extracted from varying number of MDA cells (D) or MCF cells (E) (mean±max deviation, n=3). Absorbance of the solution with PMP suspension resulting from the control sample was used as the reference.

DESCRIPTION OF THE EMBODIMENTS

Figure 1A:
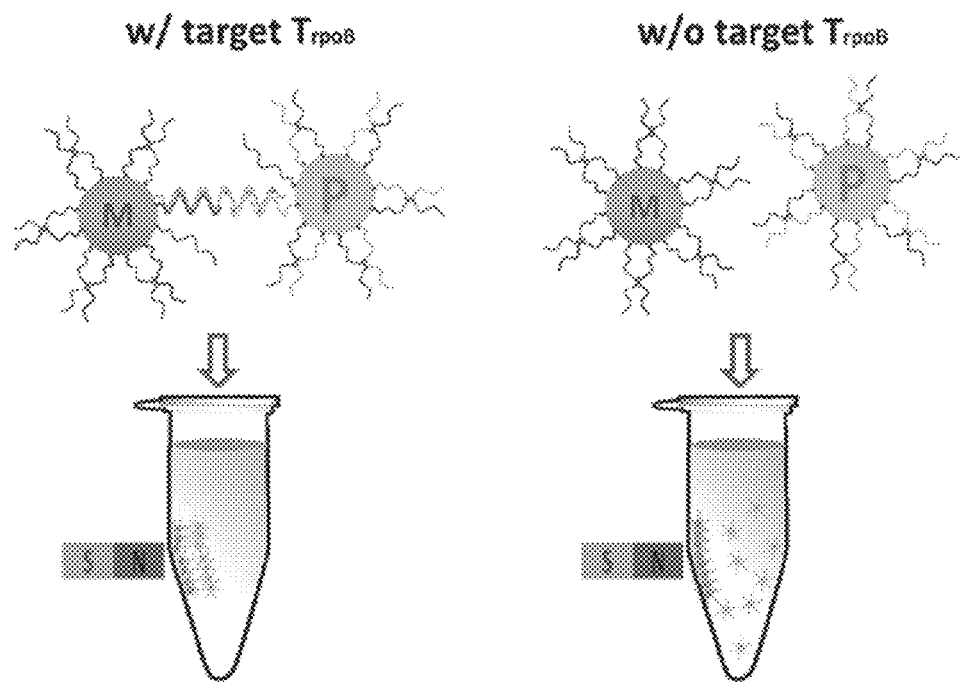
FIG. 1A is a schematic diagram showing the operating principle of the method of the present invention. In particular, two types of microparticles were used: magnetic microparticles (MMPs) loaded with both the first probe and a blocker sequence ($P1_{rpoB}$+pagA) and polystyrene microparticles (PMPs) loaded with the second probe and a blocker sequence ($P2_{rpoB}$+pagA).

The following preparations and examples are given to enable those skilled in the art to more clearly understand and to practice the present invention. They should not be considered as limiting the scope of the invention, but merely as being illustrative and for representing preferred embodiments thereof. The technical terms used in the present patent application have the meaning as commonly understood by a respective skilled person unless specifically defined otherwise.

Unless otherwise defined, all technical terms used herein have the same meaning as commonly understood by one skilled in the art to which the invention belongs.

As used herein, "comprising" means including the following elements or components but not excluding others. "Essentially consisting of" means that the material or compound consists of the respective element or components along with usually and unavoidable impurities such as side products and components usually resulting from the respective preparation or method for obtaining the material such as traces of further components or solvents. "Consisting of" means that the material solely consists of, i.e. is formed by the respective element or component. As used herein, the forms "a," "an," and "the," are intended to include the singular and plural forms unless the context clearly indicates otherwise.

The present invention relates in a first aspect to a method for determining the presence or amount of a target nucleic acid sequence in a sample, comprising steps of:

(a) adding a magnetic particle loaded with a first probe and a polystyrene particle loaded with a second probe to the sample and applying conditions such that the target nucleic acid sequence in the sample binds to the loaded magnetic particle and to the loaded polystyrene particle to form a complex comprising the target nucleic acid sequence bound to the loaded magnetic particle and to the loaded polystyrene particle;

(b) applying a magnetic force to separate the complex from the mixture of step (a);

(c) determining at least one of a physical feature of the mixture after separating the complex in step (b) or the amount of the complex separated in step (b).

The terms "target nucleic acid sequence", "target nucleic acid" and "target sequence" are used herein interchangeably and refer to a nucleic acid sequence of interest for the determination. It generally includes a DNA sequence, or a RNA sequence. The presence or amount of it is preferably suitable for indicating a disease or a health condition of a subject. The subject may be an animal such as a human, a plant or a cell population. The subject is most preferably a human. In general, the target nucleic acid sequence includes at least a region that can be recognized by a probe which has a region complementary to the target nucleic acid sequence. The target nucleic acid sequence may be derived from an animal, a plant, a bacterium or a virus. In an embodiment, the target nucleic acid sequence is a micro-RNA which is present in the blood and suitable for diagnosis or prognosis of cancer, for example breast cancer. In another embodiment, the target nucleic acid sequence is suitable for diagnosis or prognosis of an invasive disease such as malaria caused by the parasite *P. falciparum* which produces a disease-indicative protein—*Plasmodium falciparum* histidine rich protein (pf HRPII). The determined amount of the target nucleic acid sequence encoding at least a part of this protein is compared with a reference value. The target nucleic acid sequence in the present invention may be an oligonucleotide. The term "oligonucleotide" as used herein refers to a short single strain of DNA or RNA sequence with two or more nucleotides. In general, it ranges from a few, e.g. 2 to 30, to several hundred or more nucleotides.

The term "sample" refers to a biological sample obtained from a subject, e.g. a patient, or from a tissue of a subject such as a portion of an organ or cells. This includes, but is not limited to, blood, serum, plasma and saliva samples. In addition, it may also refer to a sample collected from an environment which is particular of interest for examining the quality of an environment and quantity of viral component in the environment.

The term "probe" as used herein means a single strand nucleic acid sequence which can bind to the target nucleic acid sequence or another sequence through complementary base pairing. In the present invention, the probe is immobilized on particles such as a magnetic particle, a polystyrene particle and/or a gold particle and has a portion exposed to the surrounding environment so as to be recognized by the target nucleic acid sequence or another sequence. The probe is loaded on the particles. The terms "loading" and "load" used in the present invention include, but are not limited to, covalently binding or non-covalently binding the probe to an optionally coated particle. Non-covalently binding includes, but is not limited to, biological interaction such as avidin-biotin interaction, ionic bonding, and metallic bonding. In an embodiment, the probe is covalently bound to a probe-binding coating on the particle. In another embodiment, the probe is bound to the particle through a sulfur-gold bonding; in yet another embodiment, the probe is bound to a probe-binding coating on the particle through an avidin/streptavidin-biotin interaction. The probe used in the present invention may additionally include a compound or functional group for enhancing its stability in the sample or mixture, a fluorescent compound, a dye compound or the like.

The term "particle" as used herein means a preferably spherical object such as a sphere or bead.

Unless otherwise specified, "diameter" as used for particles or the island of three-dimensional hydrogel in the present patent application preferably refers to the Feret (or Feret's) diameter at the thickest point of such particle or island. The Feret diameter is a measure of an object size along a specified direction and can be defined as the distance between the two parallel planes restricting the object perpendicular to that direction. The Feret diameter can be determined, for example, with microscopic methods. I.e. if the Feret diameters measured for the different directions of the particle or island differ, the "diameter" referred to in the present patent application always refers to the highest value measured. "Average diameter" refers to the average of "diameter" preferably measured with at least 10 particles.

The term "magnetic particle" refers to a particle which can be attracted by a magnetic field. In the present invention, the magnetic particle preferably has an average diameter of at most 1000 µm, in particular of at least 0.1 µm to less than 1000 µm, also referenced as magnetic microparticle (MMP). Preferably, the magnetic particle has an average diameter of from about 0.5 µm to about 100 µm. The magnetic particle may have an average diameter of about 0.5 µm to 20 µm, preferably about 0.6 µm to about 10 µm, more preferably about 0.8 µm to about 5 µm. The magnetic particle can be obtained from commercial suppliers and the ordinary of skill in the art is also aware of methods for preparing it.

The term "polystyrene particle" refers to a particle comprising or essentially consisting of polystyrene. Polystyrene means an aromatic polymer made from a monomer styrene having the formula (I).

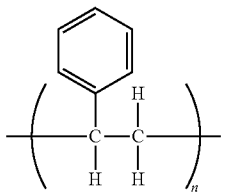

Formula (I)

n is an integer of more than 1, usually more than 10. In the present invention, the polystyrene particle comprises or essentially consists of polystyrene and has an average diameter of at most 1000 µm, in particular of at least 0.1 µm to less than 1000 µm, also referenced as polystyrene microparticle (PMP). Preferably, the polystyrene particle has an average diameter of from about 0.5 µm to about 100 µm. The polystyrene particle may have an average diameter of about 0.5 µm to 20 µm, preferably about 0.6 µm to 10 µm, more preferably about 0.8 µm to 5 µm. The polystyrene particle can be obtained from commercial suppliers and the ordinary skill in the art is also aware of methods for preparing it.

It is advantageous that polystyrene particle in the present invention offers a stable suspension for a mixture having biomolecules which may be interfering. Accordingly, the application of polystyrene particle enhances the sensitivity and specificity of the methods described herein without being affected by the interfering biomolecules in the sample. The micro-meter size of it further contributes to an easy and direct visual determination of the presence of the target nucleic acid sequence in a sample. In particular, the relatively larger size of the polystyrene particle offers a greater change in the physical feature, in particular in the light transmission and solution turbidity.

Such a change is caused by Mie scattering that can effectively attenuate light transmission with significantly enhanced extinction coefficient.

According to the method of the present invention, each of the magnetic particle and the polystyrene particle is coated with a probe-binding compound before loading the respective probe. In an embodiment, the probe-binding compound is a biotin-binding compound that can specifically bind to biotin with a strong non-covalent avidin/streptavidin-biotin interaction. Biotin is a vitamin which is present in all living cells and is important for a range of biological processes including cell growth. It is small in size and therefore it will not significant affect the sample in an assay. The biotin-binding compound is preferably selected from avidin, streptavidin and neutravidin which are natural or artificial proteins derived from animals or bacteria. These proteins have a high affinity towards biotin and form an avidin-biotin linkage or a streptavidin-biotin linkage. Accordingly, having a coating comprising or essentially consisting of a biotin-binding compound on the magnetic particle and on the polystyrene particle, these particles can then be easily loaded with the respective biotinylated probe. The term "biotinylated probe" refers to a probe further comprising biotin, for example a nucleic acid sequence linked to biotin. The term "linked" means in particular covalently bound.

The term "coating" used herein means a layer covering at least a part of the particle, in particular a significant part of the particle. In an embodiment of the present invention, streptavidin is comprised in the coating of the magnetic particle and of the polystyrene particle. The coated magnetic particle and the coated polystyrene particle preferably have at least 50% surface covered by streptavidin, preferably more than 55%, more than 60%, more than 70%, or more than 80% covered by streptavidin. The ordinary skill in the art is aware of methods of preparing the coated magnetic particle and the coated polystyrene particle.

In the method of the present invention, the magnetic particle and the polystyrene particle, which are preferably already provided with a probe-binding coating, are loaded with the respective probe for capturing the target nucleic acid sequence in the sample. In particular, a first probe is loaded on the magnetic particle and a second probe is loaded on the coated polystyrene particle. Preferably, the first and second probes are at least partially complementary single strand nucleic acid sequences of the target nucleic acid sequence and are different. In an embodiment, the first probe includes a nucleic acid sequence at least partially complementary to the sequence adjacent to or at the 5' end of the target nucleic acid sequence, and the second probe includes a nucleic acid sequence at least partially complementary to the sequence adjacent to or at the 3' end of the target nucleic acid sequence, or vice versa.

Accordingly, when the first and second probes hybridize with the target nucleic acid sequence, the magnetic particle and the polystyrene particle bind to the target nucleic acid sequence and form a complex which may have a sandwich-like structure, i.e. the magnetic particle is linked to the polystyrene particle through the target nucleic acid sequence in between them.

In a preferred embodiment of the present invention, the first probe is a biotinylated nucleic acid sequence and the magnetic particle is coated with streptavidin. For loading the first probe to the magnetic particle, one or more magnetic particles are mixed with a mixture containing the first probe. The loading is preferably performed by incubating the mixture at a temperature of about 20° C. to 25° C. for at least 10 min, preferably at least 20 min, more preferably at least 30 min, accompanied by shaking. The loaded magnetic particles are then collected, and preferably purified.

The loaded magnetic particles are preferably purified by rinsing with a washing buffer to remove unloaded first probe from the magnetic particles, and are collected with a magnet or a device equipped with a magnet, e.g. a magnetic separation rack.

The washing buffer can be readily prepared and selected by the person skilled in the art for achieving the washing purpose.

The second probe is preferably a biotinylated nucleic acid sequence and the polystyrene particle is coated with streptavidin. For loading the second probe to the polystyrene particle, one or more polystyrene particles are mixed with a mixture containing the second probe. The loading is preferably performed by incubating the mixture at a temperature of about 20° C. to 25° C. for at least 10 min, preferably at least 20 min, more preferably at least 30 min, accompanied by shaking. The loaded polystyrene particles are then collected and preferably purified. The loaded polystyrene particles are preferably purified by rinsing with a washing buffer to remove unloaded second probe form the polystyrene particles, and are collected by using a centrifuge.

In another embodiment of the present invention, the method further includes a step of loading a blocker nucleic acid sequence, also referred to as a blocker sequence, to at least one of the magnetic particle or the polystyrene particle. The blocker sequence is an oligonucleotide having a region complementary to the first probe and another region complementary to the second probe. In particular, the binding energy between the blocker sequence and the first probe and the binding energy between the blocker sequence and the second probe are lower than that between the first and second probe. Accordingly, it can partially hybridize with the first and second probe respectively to reduce non-specific binding between the first and second probe. It is of particularly advantageous when the first probe has a sequence complementary to the second probe which leads to non-specific binding between the probes.

Preferably, the blocker sequence is linked to biotin and then loaded on the magnetic particle and the polystyrene particle. The blocker sequence then binds to the first or second probe before coming into contact with the target nucleic acid sequence. When the target nucleic acid sequence is present, the relatively weak binding between the blocker sequence and the first or second probe diminished and the first or second probe will be exposed to the target nucleic acid sequence for hybridization. The application of the blocker sequence is advantageous in that the non-specific binding between the first and second probe can be significantly reduced.

Step (a) of the method preferably comprises steps of:
(i) adding the loaded magnetic particle to the sample and applying conditions such that the target nucleic acid sequence in the sample binds to the loaded magnetic particle;
(ii) separating the loaded magnetic particle optionally bound to the target nucleic acid sequence from the mixture of step (i) by applying a magnetic force;
(iii) adding a mixture containing the loaded polystyrene particle to the loaded magnetic particle separated in step (ii), and applying conditions such that the target nucleic acid sequence in the bound loaded magnetic particle binds to the loaded polystyrene particle to form the complex.

In step (i), the conditions applied for binding between the target nucleic acid sequence and the loaded magnetic particle comprise stirring the mixture at a temperature of about 20° C. to about 25° C. for at least 10 min, preferably at least 20 min, more preferably at least 30 min and optionally with shaking.

In step (ii), a magnetic force preferably created by a magnet or a device equipped with a magnet is used to separate the magnetic particle including bound magnetic particles and unbound magnetic particles from the mixture. For example, the magnetic particles are attracted to a side of the reaction container e.g. a tube, and the rest of the mixture is removed from the reaction container. Optionally a washing buffer is added to rinse the magnetic particles and then removed after rinsing.

In step (iii), the conditions applied for the binding between the target nucleic acid sequence and the loaded polystyrene particle comprise stirring the mixture at a temperature of about 20° C. to about 25° C. for at least 10 min, preferably at least 20 min, more preferably at least 30 min. Subsequently, the complex having the target nucleic acid sequence bound to the loaded magnetic particle and the loaded polystyrene particle is formed.

In another embodiment, the loaded magnetic particle and the loaded polystyrene particle are added to the sample simultaneously for binding with the target nucleic acid sequence under the conditions as described above.

Step (b) of the method refers to the separation of the complex from the mixture. In particular, a magnetic force generated by a magnetic or a device equipped with a magnet is used to attract the complex to a side of the reaction container.

In an embodiment of the present invention, step (c) further comprises steps of:
(i) isolating the complex separated in step (b), optionally purifying the complex and suspending it in a mixture;
(ii) introducing the mixture after step (i) to a device having an inlet port and a micro-channel, wherein the micro-channel comprises a neck portion with a diameter smaller than the size of the loaded polystyrene particle;
(iii) determining the amount of the polystyrene particle being trapped in the micro-channel, and optionally comparing the determined amount with a reference value.

The purification of step (i) may be performed by rinsing with a washing buffer. A mixture containing a buffer for maintaining certain pH and configuration of the complex may be added to the separated complex for subsequent determination. Optionally, the separated complex is dried after purification, in particular freeze dried to release polystyrene particles from the complex.

This embodiment of the present invention in particular uses a device suitable for determining the amount of polystyrene particles in the separated complex. The device can include:
an inlet port for introducing the mixture;
a mixing zone for mixing the particles in the mixture;
a first collection zone subjected to a magnetic field for collecting magnetic particles;
a second collection zone with a micro-channel for collecting the polystyrene particles present in the mixture;
a capillary pump for generating a capillary force to move the mixture from the inlet port to a reservoir; and
the reservoir.

Based on the capillary flow, the mixture is transported from the inlet port to the mixing zone which is preferably arranged with a serpentine channel for thoroughly mixing based on the exchange of fluidic layers in the laminar flow at micro-scale, then to the first collection zone. All magnetic particles present in the mixture are attracted and immobilized in the first collection zone and the rest of the mixture enters the second collection zone. The second collection zone has a micro-channel configured to have a neck portion with a diameter smaller than the size of the loaded polystyrene particle. As such, any polystyrene particle enters the second collection zone is then trapped in the micro-channel while the rest of the mixture can still pass through the micro-channel to the reservoir for removal. The micro-channel is preferably marked with indicia for direct measurement of the amount of polystyrene particle being trapped in the micro-channel. Such a device allows rapid measurement of the amount of the polystyrene particles in the complex. Preferably by comparing the determined amount with a reference value, the corresponding amount of the target nucleic acid sequence can be calculated.

Step (c) of the method can alternatively or additionally comprise steps of determining a physical feature of the mixture after separating the complex. Preferably, the physical feature includes, but is not limited to the colour, turbidity and spectral absorbance of the mixture after separating the complex in step (b). The person skilled in the art is aware of suitable methods for determining the colour change of the mixture, change in solution turbidity and spectral absorbance of the mixture. For example, these one or more of these physical features may be determined by UV-VIS spectrometry. Other methods known in the art for these measurements are also suitable. The measured value can preferably be compared with a reference value to interpret the presence or exact amount of the target nucleic acid in the sample.

For example, in an embodiment of the present invention, the more complexes formed in step (a), the larger reduction in turbidity of the mixture after separating the complex in step (b). Accordingly, the present invention makes use of Mie scattering effect and magnetophoretic effect of the complex and offers an easily manipulated and time-saving approach for determining the presence or amount of target nucleic acid in a sample. In addition, the method as described herein is compatible with a multiplex sample such as whole blood sample. The highly stable polystyrene particle offers exceptionally suspension stability in the mixture for measurement.

In another aspect of the present invention, the method for determining the presence or amount of a target nucleic acid sequence in a sample comprises steps of:

(a) adding a first magnetic particle loaded with a first probe and a gold particle loaded with a second probe to the sample and applying conditions such that the target nucleic acid sequence in the sample binds to the first loaded magnetic particle and to the loaded gold particle to form a first complex comprising the target nucleic acid sequence bound to the first loaded magnetic particle and to the loaded gold particle;

(b) applying a magnetic force to separate the first complex from the mixture of step (a);

(c) separating the loaded gold particle from the first complex separated in step (b);

(d) adding a second magnetic particle loaded with a third probe and a polystyrene particle loaded with a fourth probe to the loaded gold particle of step (c) and applying conditions such that the second probe of the loaded gold particle binds to the second loaded magnetic particle and to the loaded polystyrene particle to form a second complex comprising the second probe of the loaded gold particle bound to the second loaded magnetic particle and to the loaded polystyrene particle; and (e) applying a magnetic force to separate the second complex from the mixture of step (d);

(f) determining at least one of a physical feature of the mixture after separating the second complex in step (e) or the amount of the second complex separated in step (e).

This method includes the application of a gold particle for the purpose of further improving the sensitivity compared to the embodiments of the method described before. The "gold particle" used herein refers to a particle comprising, in particular essentially consisting of gold. In the present invention, the gold particle preferably has an average diameter of at most 1000 nm. Preferably, the gold particle has an average diameter in the nano-meter range, i.e. from 0.1 nm to less than 100 nm and thus is also referred to as gold nanoparticle (AuNP). The gold particle may have an average diameter of about 1 nm to 90 nm, preferably about 10 nm to 80 nm, more preferably about 20 nm to 70 nm. In an embodiment, the gold particle has an average diameter of about 30 nm. The gold particle can be obtained from commercial suppliers.

A nano-scale of the gold particle allows for an enhanced sensitivity of the method. This is exceptionally advantageous for the detection of target nucleic acid sequence in low abundance. The gold particle can be loaded with a probe.

The first magnetic particle is loaded with a first probe and the gold particle is loaded with a second probe; a second magnetic particle is loaded with a third probe and a polystyrene particle is loaded with a fourth probe. Preferably, the first and second probe are at least partially complementary single strand nucleic acid sequences of the target nucleic acid sequence and are different. In an embodiment, the first probe includes a nucleic acid sequence at least partially complementary to the sequence adjacent to or at the 5' end of the target nucleic acid sequence, and the second probe includes a nucleic acid sequence at least partially complementary to the sequence adjacent to or at the 3' end of the target nucleic acid sequence, or vice versa.

In a preferred embodiment of the present invention, the first probe is a biotinylated nucleic acid sequence and the first magnetic particle is coated with streptavidin. The loading method of the first probe to the magnetic particle is as described above.

The second probe is preferably a nucleic acid sequence linked to a polyethylene glycol (PEG) and a thiol group. The thiol group of the second probe binds to the gold particle through a sulfur-gold bonding. For loading the second probe to the gold particle, the second probe is firstly activated by Tris (2-carboxyethyl) phosphine (TCEP) for at least 30 min, or at least 1 h, and then added to one or more gold particles at a temperature of about 20° C. to about 25° C. for at least 10 h, at least 12 h, at least 14 h or at least 16 h. Followed by subsequent dilution steps and aging process for at least 24 h, at least 36 h or at least 40 h, the loaded gold particle is purified and collected preferably through centrifugation.

Another two probes applied include a third probe loaded to a second magnetic particle and a fourth probe loaded to a polystyrene particle. The third probe and the fourth probe are preferably single strand nucleic acid sequences at least partially complementary to the second probe loaded to the gold particle. In particular, the third probe and the fourth probe are different and bind to the second probe at different positions e.g. one binds adjacent to the 5' end of the sequence and the other binds to a 3' end of the sequence. Preferably, the third and fourth probes are biotinylated sequences for loading on the second magnetic particle and the polystyrene particle. The conditions for loading the probes on the particles are as described above.

The application of a gold particle is additionally advantageous in that it provides an amplification effect to the amount of the target nucleic acid sequence in the sample.

The gold particle is capable of loading a great number of probes on its particle surface and these probes can thus serve as a target for the polystyrene particle to bind to. Accordingly, a substantial amount of polystyrene particles is bound to the second probe for forming a second complex with the second probe bound to the second magnetic particle and the polystyrene particle. Such an amplified amount of polystyrene particles offers a sharp change in the physical properties such as the turbidity and spectral absorbance in step (f) after separating the second complex from the mixture.

Step (a) of the method according to this second aspect of the present invention comprises steps of:

(i) adding the first loaded magnetic particle to the sample and applying conditions such that the target nucleic acid sequence in the sample binds to the first loaded magnetic particle;

(ii) separating the first loaded magnetic particle optionally bound to the target nucleic acid sequence from the mixture of step (i) by applying a magnetic force;

(iii) adding a mixture containing the loaded gold particle to the separated first loaded magnetic particle, and applying conditions such that the target nucleic acid sequence in the bound first loaded magnetic particle binds to the loaded gold particle to form the complex.

In step (i), the conditions applied for binding between the target nucleic acid sequence and the loaded first magnetic particles preferably comprise stirring the mixture at a temperature of about 20° C. to about 25° C. for at least 10 min, preferably at least 20 min, more preferably at least 30 min.

In step (ii), a magnetic force generated by a magnet or a device equipped with a magnet is used to separate the magnetic particles including bound magnetic particles and unbound magnetic particles from the mixture. Optionally a washing buffer is added to rinse the magnetic particles and then the washing buffer is removed after rinsing.

In step (iii), the conditions applied for binding between the target nucleic acid sequence and the loaded gold particle preferably comprise stirring the mixture at a temperature of about 20° C. to about 25° C. for at least 10 min, preferably at least 20 min, more preferably at least 30 min. Subsequently, the first complex having the target nucleic acid sequence bound to the loaded first magnetic particle and the loaded gold particle is formed.

In another embodiment, the loaded first magnetic particle and the loaded gold particle are added to the sample simultaneously for binding to the target nucleic acid sequence preferably under the conditions as described above.

In step (b) of the method, the separated first complex is preferably isolated from the mixture by applying the magnetic force and thus the remaining unreacted components are removed.

In step (c), the first complex is preferably suspended in a mixture or solution essentially consisting of water. The resultant mixture is then heated to a temperature of at least 50° C., at least 60° C. or preferably to at least 70° C. to separate the loaded gold particle from the first complex release it into the mixture. The thiol-gold bonding remains unchanged during the heat treatment and thus the second probe is still firmly loaded on the gold particle.

In step (d), a second complex is formed by binding the second magnetic particle loaded with the third probe and the polystyrene particle loaded with the fourth probe to the second probe on the gold particle. As described above, the third probe and the fourth probe are preferably sequences at least partially complementary to the second probe and hybridize according to the conditions as described before.

Subsequently, the second complex is separated from the mixture by applying a magnetic force to attract the second complex to a side of the reaction container for observing the change in turbidity or measuring the difference in spectral absorbance. In an embodiment, in order to minimize any non-specific binding between the probes, a blocker sequence as described above can be applied. I.e. the second loaded magnetic particle and the loaded polystyrene particle are additionally loaded with a blocker nucleic acid sequence having a region at least partially complementary to the third probe and another region at least partially complementary to the fourth probe.

In a further embodiment, a device suitable for determining the amount of polystyrene particles collected is applied in step (f). The device, as described before, includes: an inlet port for introducing the mixture; a mixing zone for mixing the particles in the mixture; a first collection zone subjected to a magnetic field for collecting magnetic particles; a second collection zone with a micro-channel for collecting the polystyrene particles present in the mixture; a capillary pump for generating a capillary force to move the mixture from the inlet port to a reservoir; and the reservoir. Accordingly, step (f) of this method further includes steps of (i) isolating the separated second complex, optionally purifying the second complex and suspending it in a mixture;

(ii) introducing the mixture after step (i) to a device having an inlet port and a micro-channel, wherein the micro-channel comprises a neck portion with a diameter smaller than the size of the loaded polystyrene particle;

(iii) determining the amount of the loaded polystyrene particle from the second complex being trapped in the micro-channel, and preferably comparing the determined amount with a reference value.

Alternatively or additionally, a physical feature can be determined in the mixture after separating the second complex in step (e) from the mixture such as the colour or the turbidity as described above.

The present invention also refers to a kit. In particular, the kit of the present invention includes a magnetic particle loaded with a probe; and a polystyrene particle loaded with a probe. The probe loaded on the magnetic particle and the probe loaded on the polystyrene particle are different single strand nucleic acid sequences linked to biotin. The magnetic particle and the polystyrene particle are in particular those as described above for the methods of the present invention.

In an embodiment of the present invention, the kit further comprises a gold particle loaded with a probe.

The loaded magnetic particle and the loaded polystyrene particle can further comprise a blocker sequence as described above for the methods of the present invention.

The present invention can in particular be used for in the diagnosis or prognosis of a disease or a health condition of the subject. The presence or amount of one or more target nucleic acid sequences is preferably indicative of a health condition or progress of a disease or illness. For example, the disease or abnormal health condition means presence or an abnormal amount of the nucleic acid sequence compared to that in a healthy subject. Accordingly, the present invention also directs to a method of diagnosing or prognosing a disease in a subject.

Example 1

Figure 1B:
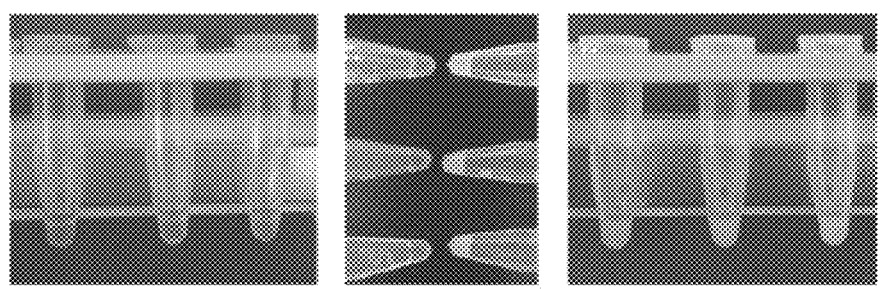
FIG. 1B shows optical images showing the changes in light transmission in response to the presence of the target, $T_{rpoB}$. When $T_{rpoB}$ was present, the solution became transparent (left); when target $T_{rpoB}$ was absent, the solution remained opaque (right).

Method of determining the presence or amount of a target nucleic acid sequence by using a magnetic particle and a polystyrene particle FIG. 1 demonstrates an example of the present invention comprising employing magnetic particles (MMPs) loaded with a first probe, $P1_{rpoB}$, and polystyrene particles (PMPs) loaded with a second probe, $P2_{rpoB}$. The first and second probes are partially complementary to the target nucleic acid sequence $T_{rpoB}$. A blocker sequence, pagA, was also loaded on the magnetic particles and the polystyrene particles for further reducing the non-specific binding between the first and second probe.

Figure 8:
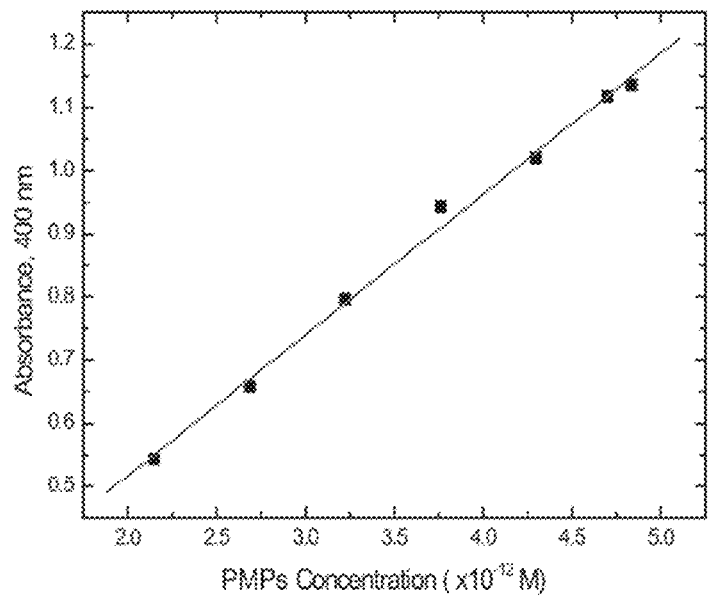
FIG. 8 shows UV-Vis spectral absorbance ($A_\lambda$) of PMP suspension with varied concentration (c). The slope factor of linear fitting is $2.2285\times10^{11}$ $M^{-1}$ ($R^2$=0.995). According to Lambert-Beer Law ($A_\lambda$=εcL), the extinction coefficient (ε) can be determined as $4.457\times10^{12}$ $M^{-1}cm^{-1}$, where the slope factor is $A_\lambda$/c and the path length (L) of the UV-Vis spectrometer (BioDrop μLITE, UK) is 0.05 cm.

The change in turbidity caused by the Mie scattering due to the size of the PMPs was observed. Such a change in turbidity attenuated the light transmission with a significantly enhanced extinction coefficient compared to AuNPs (~3 orders of magnitude, FIG. 8).

According to the results obtained which will be described below, PMPs showed an improved stability in their dispersion, allowed for a rapid modification through a streptavidin-biotin link and enhanced compatibility with complex bio-fluids, i.e. in complex samples. Based on the enhanced light scattering effect and stability, this method achieved a limit of detection at 16 pM by the naked eye and at 4 pM by spectrometry. In addition, it is compatible with multiplex assays and detection in complex bio-fluids, such as whole blood or a pool of nucleic acids, without purification in advance. With its fast procedure, low instrumentation requirement and advantageous sensitivity, this method provides an ideal solution for applications in resource-limited settings.

Oligonucleotide Sequences

Single-stranded oligonucleotides were purchased from Sangon Biotech Ltd (Shanghai, China) and dissolved in Tris-ethylenediaminetetraacetic acid (Tris-EDTA) buffer. The sequences are listed in Table 1. Oligonucleotide probes, $P1_{rpoB}$ pairing with $P2_{rpoB}$ and $P1_{capC}$ pairing with $P2_{capC}$, were designed with a sequence partially complementary to the target oligonucleotides $T_{rpoB}$ and $T_{capC}$, respectively, in juxtaposition. $T_{rpoB}$+30A and $T_{rpoB}$+60A are targets of which 30 bases and 60 bases of adenine (A) were inserted in the middle of the sequence of $T_{rpoB}$, respectively. The SNP A, SNP G and SNP C oligonucleotides were designed with single-base mismatches (shown in bold italics underlined in Table 1) compared to $T_{rpoB}$. The probes and the auxiliary blocker sequence, pagA, were biotinylated, such that they can spontaneously attach to streptavidin-coated MMPs of 0.90 μm (CM01N, Bangslab, USA) and streptavidin-coated PMPs of 1.04 μm (CP01F, Bangslab, USA) and 0.97 μm.

TABLE 1

The sequences of the single-strand oligonucleotides

| Strand name | Comprises SEQ ID NO. | Structure of the strand |
|---|---|---|
| $T_{rpoB}$ | 1 | 5'-ACTTGTGTCTCGTTTCTTCGATCCAAAGCG-3' |
| $P1_{rpoB}$ | 2 | 5'-AAACGAGACACAAGT-/biotin/-3' |
| $P2_{rpoB}$ | 3 | 5'-/biotin/CGCTTTGGATCGAAG-3' |
| pagA | 4 | 5'-CTCGAACTGGAGTGA-/biotin/-3' |
| $T_{capC}$ | 5 | 5'-ATGCCATTTGAGATTTTGAATTCCGTGGT-3' |
| $P1_{capC}$ | 6 | 5'-AATCTCAAATGGCAT-/biotin/-3' |
| $P2_{capC}$ | 7 | 5'-/biotin/-ACCACGGAATTCAAA-3' |
| SNP A | 8 | 5'-ACTTGTGACTCGTTTCTTCGATCCAAAGCG-3' |
| SNP G | 9 | 5'-ACTTGTGGCTCGTTTCTTCGATCCAAAGCG-3' |
| SNP C | 10 | 5'-ACTTGTGCCTCGTTTCTTCGATCCAAAGCG-3' |
| $T_{rpoB}$ + 30A | 11 | 5'-ACTTGTGTCTCGTTT - $A_{30}$ - CTTCGATCCAAAGCG-3' |
| $T_{rpoB}$ + 60A | 12 | 5'-ACTTGTGTCTCGTTT - $A_{60}$ - CTTCGATCCAAAGCG-3' |

Figure 2:
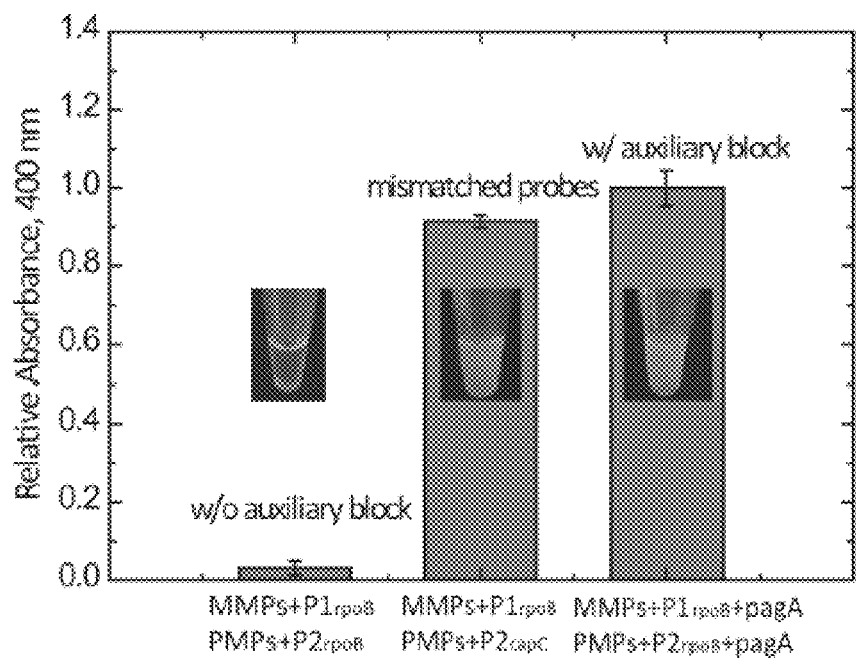
FIG. 2 shows the optical images and relative UV-Vis spectral absorbance at 400 nm for MMPs loaded with $P1_{rpoB}$ and PMPs loaded with $P2_{rpoB}$, MMPs loaded with mismatched $P1_{rpoB}$ and PMPs loaded with mismatched $P2_{rpoB}$, MMPs loaded with $P1_{rpoB}$+pagA and PMPs loaded with $P2_{rpoB}$+pagA wherein an auxiliary oligonucleotide pagA, also referenced as a blocker sequence was applied to block the partial hybridization between $P1_{rpoB}$ and $P2_{rpoB}$. The absorbance of the suspension resulting from the loading of the blocker sequence was used as the reference. The relative absorbance is derived from repeated experiments (mean±SEM, n=3).

The results in FIG. 2 show that there was some non-specific binding between the probes. The partial complementary sequence between $P1_{rpoB}$ and $P2_{rpoB}$, "5'-AAA-3'" on $P1_{rpoB}$ pairing with "3'-TTT-5'" on $P2_{rpoB}$ or "5'-CGA-3'" on $P1_{rpoB}$ pairing with "3'-TCG-5'" on $P2_{rpoB}$, could be the reason for a spontaneous binding between MMPs and PMPs. To verify this, the modification of PMPs was changed to $P2_{capC}$, which has no sequence complementary with $P1_{rpoB}$.

After magnetic attraction, the suspension remained opaque, validating that the strong non-specific binding between $P1_{rpoB}$ and $P2_{rpoB}$ modified microparticles was due to the hybridization of partial complementary sequences.

To further reduce this non-specific binding, a biotinylated auxiliary oligonucleotide, i.e. blocker sequence, pagA was introduced. The sequence pagA was partially complementary to $P1_{rpoB}$ at "5'-CTCG-3'" and $P2_{rpoB}$ at "5'-TCGA-3'". Therefore, pagA could partially hybridize with $P1_{rpoB}$ and $P2_{rpoB}$. As such, when $T_{rpoB}$ was present, the partial hybridization denatured and $P1_{rpoB}$ and $P2_{rpoB}$ can then hybridize with $T_{rpoB}$ in juxtaposition, forming sandwich structures that make the suspension transparent through the magnetophoretic effect. To demonstrate the feasibility of this mechanism, MMPs modified with $P1_{rpoB}$ and pagA, and PMPs modified with $P2_{rpoB}$ and pagA were used. The result showed that the non-specific binding could be eliminated (FIG. 2). The binding energy for $P1_{rpoB}$+pagA and $P2_{rpoB}$+pagA were determined as −6.78 kcal mol$^{-1}$ and −6.76 kcal mol$^{-1}$ respectively. These values were lower than the binding energy between $P1_{rpoB}$ and $P2_{rpoB}$ (−5.19 kcal mol$^{-1}$), indicating that the non-specific binding due to $P1_{rpoB}$ and $P2_{rpoB}$ could be minimized when the auxiliary oligonucleotide pagA was used.

Determination of the Detection Limit

Figure 3A:
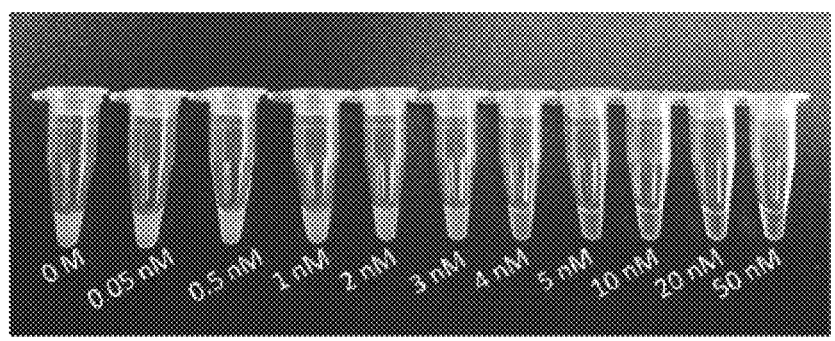
FIGS. 3A, 3B, 3C, and 3D show the detection of $T_{rpoB}$ solution of varying concentrations.
Figure 3B:
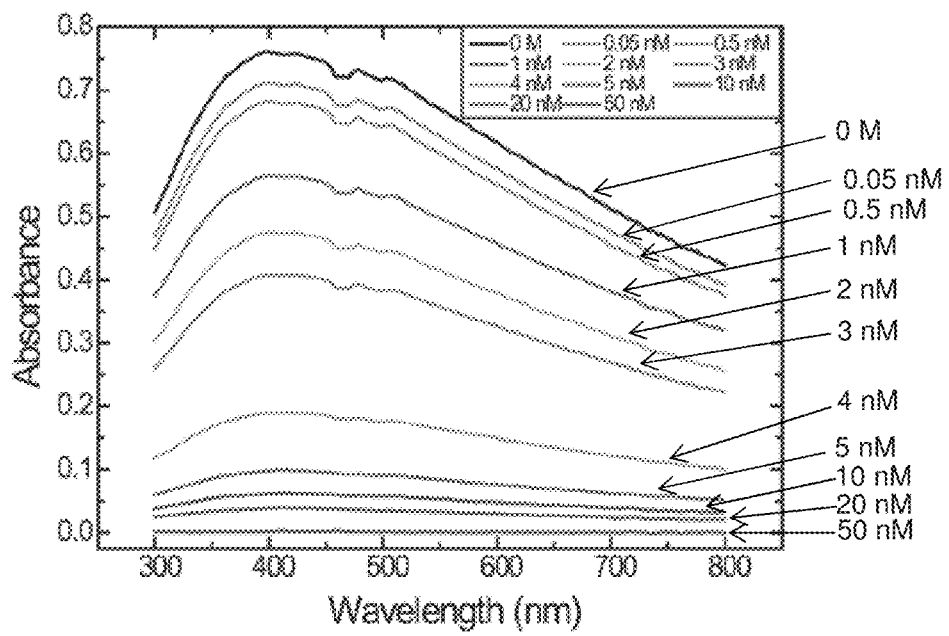
Figure 3C:
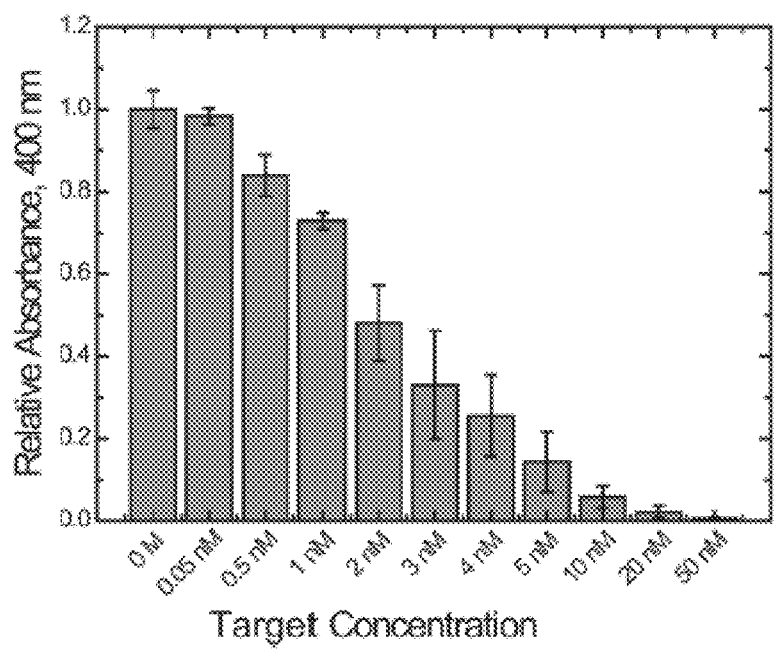
Figure 3D:
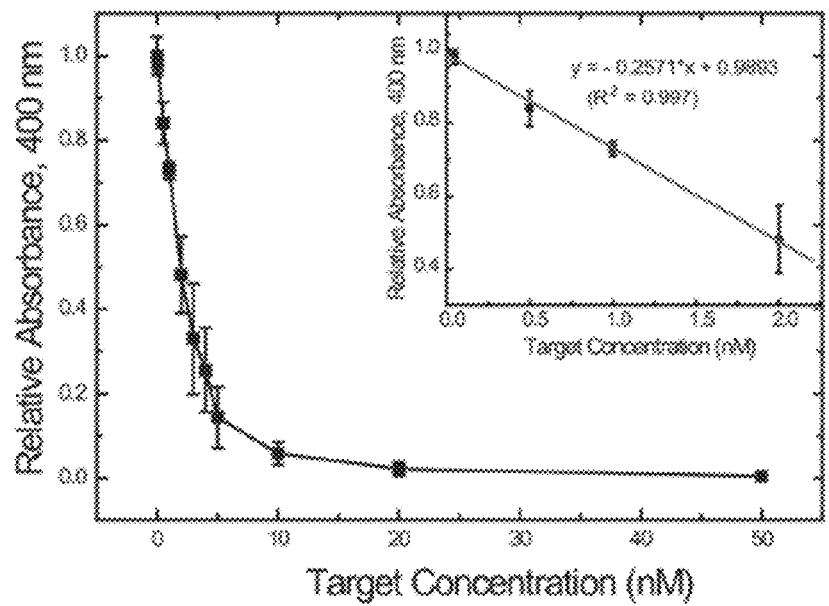

The limit of detection using 20 μl of $T_{rpoB}$ solution at various concentrations (0 M, 0.05 nM, 0.5 nM, 1 nM, 2 nM, 3 nM, 4 nM, 5 nM, 10 nM, 20 nM and 50 nM) is demonstrated in FIG. 3A. The suspension from 0 M was completely opaque. In contrast, as the concentration of $T_{rpoB}$ increased, the suspension gradually became transparent. The difference could be discriminated by the naked eye when concentrations of $T_{rpoB}$ were greater than 2 nM. Using a UV-VIS spectrometer, the spectral absorbance of the suspension was analyzed (FIGS. 3B and 3C). According to the absorbance at 400 nm, the limit of detection was 50 pM. The absorbance was inversely proportional to the concentration of $T_{rpoB}$ and had a linear range of 50 pM$^{-2}$ nM ($R_2$=0.997, FIG. 3D). Moreover, the MMPs and PMPs directly reacted with the target solution in 20 μl. Thus, the duration was only 10-30 min. When the concentration of the target oligonucleotide was high, detection was almost in real-time and was visible to the naked eye.

Figure 10:
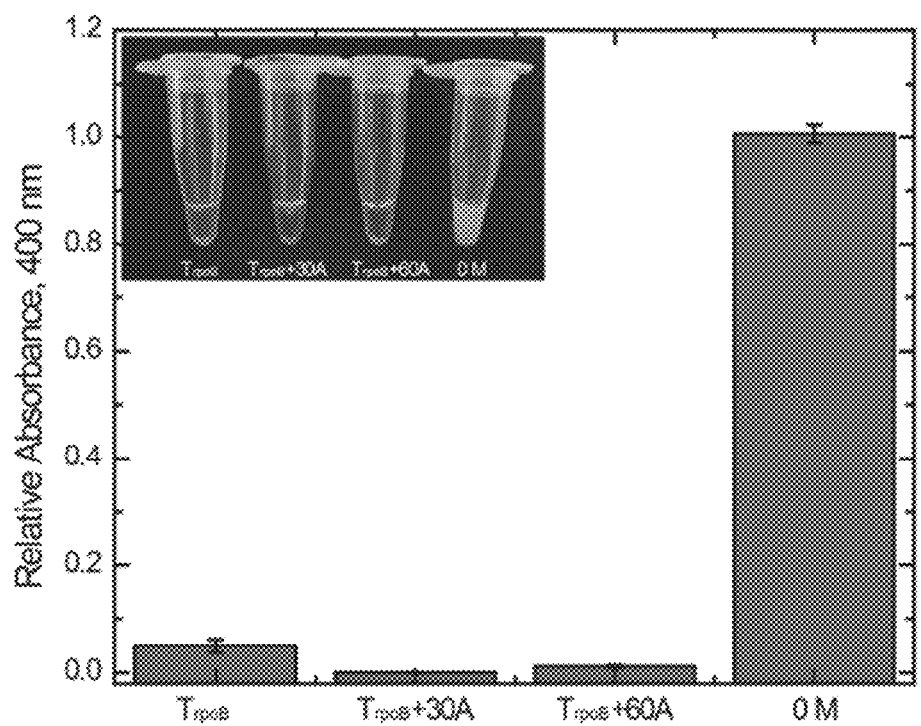
FIG. 10 shows the detection of target nucleic acid sequence with different length by showing optical images and relative UV-Vis spectral absorbance at 400 nm of the suspension resulting from 10 nM of $T_{rpoB}$, $T_{rpoB}$+30A and $T_{rpoB}$+60A, whose lengths of total bases were 30, 60 and 90, respectively. The sequences of $T_{rpoB}$+30A and $T_{rpoB}$+60A was designed by adding 30 bases and 60 bases of adenine (A), respectively, in the middle of the sequence of $T_{rpoB}$. The absorbance of the suspension resulting from the blank sample (hybridization buffer with 0M target nucleic acid sequence) was used as the reference. The relative absorbance is from repeated experiments (mean±SEM, n=3).

Moreover, the method is applicable to target oligonucleotides with a longer sequence. The sequences of $T_{rpoB}$+30A and $T_{rpoB}$+60A, of which 30 bases and 60 bases of adenine (A) were inserted in the middle of the sequence of $T_{rpoB}$, respectively. The results showed that the suspensions resulting from 10 nM of $T_{rpoB}$, $T_{rpoB}$+30A and $T_{rpoB}$+60A became all transparent and had a similar level of absorbance (FIG. 10), indicating the compatibility with the detection of targets with a longer sequence. In other words, the method of the present invention is applicable for detecting a target nucleic acid sequence having a sequence length of more than 90 nucleotide residues, too.

Modification of Microparticles

The terms "modification" and "modified" used in the examples below have the same meaning as "loading" and "loaded" as defined above.

Based on the streptavidin-biotin bonds, the MMPs were modified with $P1_{rpoB}$ and pagA, while the PMPs were modified with $P2_{rpoB}$ and pagA. Briefly, a 3.5 μl suspension of MMPs (10 mg ml$^{-1}$) was mixed with 2.5 μg $P1_{rpoB}$ and 2.5 μg pagA. A 3.5 μl suspension of PMPs (10 mg ml$^{-1}$) was mixed with 2.5 μg $P2_{rpoB}$ and 2.5 μg pagA. The mixtures were incubated for 30 min at room temperature with gentle shaking, allowing immobilization of biotinylated oligonucleotides on streptavidin-coated microparticles. Next, the MMPs and PMPs were rinsed with 200 µl of wash buffer (20 mM Tris-HCl, pH 7.5, 1 M NaCl, 1 mM EDTA, 0.0005% Trition X-100) three times to remove the residual oligonucleotides. For each washing step, the MMPs were collected using a magnetic separation rack, while the PMPs were collected using a centrifuge (13.8 g for 5 min).

$P1_{rpoB}$ and $P2_{rpoB}$ were immobilized onto streptavidin coated MMPs and PMPs, respectively, via biotin-streptavidin interactions. As such, when $T_{rpoB}$ was present, $P1_{rpoB}$ and $P2_{rpoB}$ hybridized with $T_{rpoB}$ simultaneously, forming a sandwich-like structure, MMPs-$T_{rpoB}$-PMPs. Thus, using a magnetic field, the PMPs were carried by the MMPs towards the sidewall of the reaction container, making the suspension transparent, with reference to FIG. 1B. In contrast, when $T_{rpoB}$ was absent, the PMPs were freely suspended in the solution, which made the suspension opaque due to the Mie scattering.

PMP-Based Magnetophoretic Assay with Magnetic Microparticles and Polystyrene Microparticles Added Simultaneously The modified MMPs and PMPs (35 µg each) were first mixed in 20 µl of hybridization buffer (10 mM Tris-HCl, 1 mM EDTA, 1 M NaCl, 0.2% Tween 20, pH 8.2) and the supernatant was removed after centrifugation (13.8 g for 5 min). 20 µl of hybridization buffer with varying concentrations of the target $T_{rpoB}$, $T_{rpoB}$+30A, $T_{rpoB}$+60A, SNP A, SNP G or SNP C was mixed with MMPs and PMPs for 30 min at room temperature with gentle shaking.

PMP-Based Magnetophoretic Assay with Separate Additions of Magnetic Microparticles and Polystyrene Microparticles 1500 µl of hybridization buffer with varying concentrations of target $T_{rpoB}$ was first mixed with 35 µg of MMPs for 30 min at room temperature with gentle shaking. The MMPs were then washed and separated from the suspension using a magnetic separation rack and the MMPs with $T_{rpoB}$ were mixed with the modified PMPs (35 µg) in 20 µl of hybridization buffer for 30 min with gentle shaking. Finally, a magnetic separation rack or a magnet was used to provide magnetic attraction that pulls the MMPs and MMPs-targets-PMPs towards the sidewall, allowing the solution turbidity observed by the naked eye or quantitatively analyzed using a UV-Vis spectrometer (BioDrop µLITE, UK).

Figure 4A:
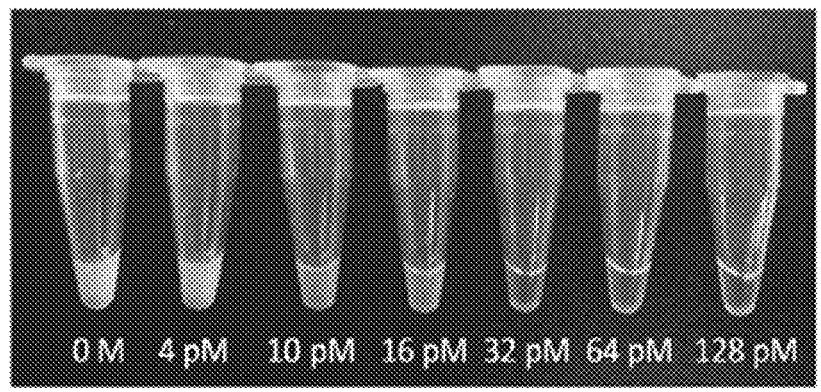
FIGS. 4A, 4B, 4C, and 4D show the detection of diluted $T_{rpoB}$ solution using optimized experimental conditions.
Figure 4B:
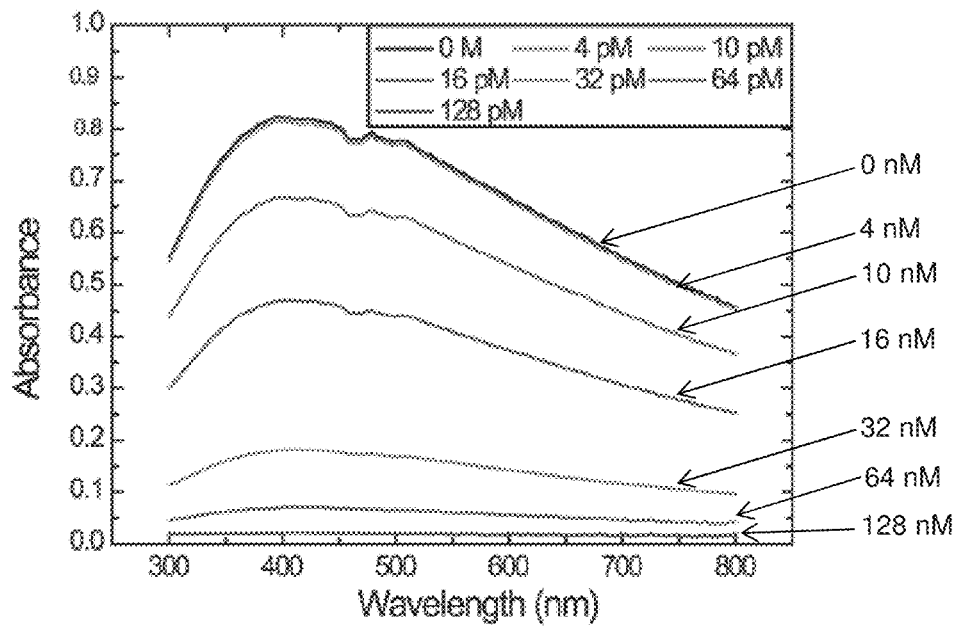
Figure 4C:
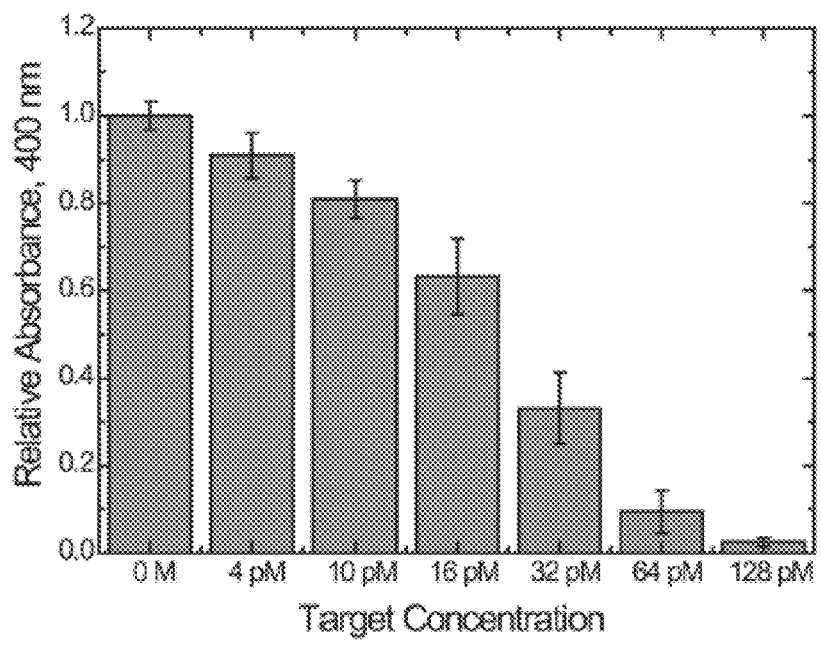
Figure 4D:
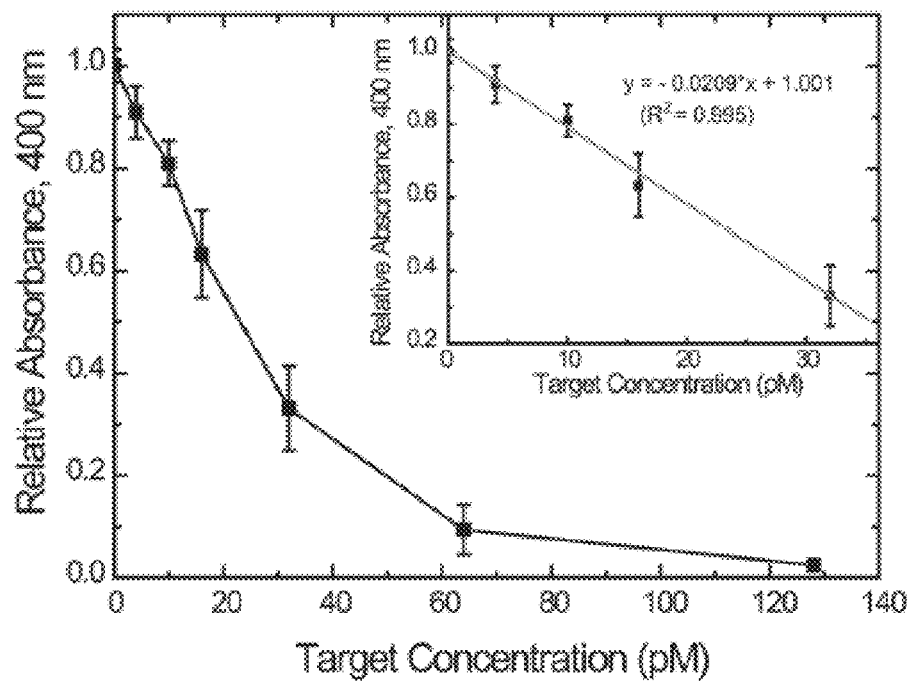

This assay was performed in two steps: (1) extracting the target oligonucleotide and (2) performing a visual detection. The MMPs were first used to extract the $T_{rpoB}$ from a diluted sample solution of a larger volume, e.g. 1500 µl. After incubation and washing, the PMPs were then introduced into the MMPs carrying the target $T_{rpoB}$, followed by visual detection of the suspension using magnetic attraction. Lower concentrations of the $T_{rpoB}$ solution were used, including 0 M, 4 pM, 10 pM, 16 pM, 32 pM, 64 pM and 128 pM. The results showed that when using MMPs for target extraction, the limit of detection was reduced to 4 pM by the spectrum analysis (FIGS. 4A and 4B) and 10 pM by visual inspection. Meanwhile, the spectral absorbance decreased as the concentration of $T_{rpoB}$ increased (FIG. 4C), with a linear range of 4 pM-128 pM detected using a UV-Vis spectrometer (FIG. 4D).

Multiplex Assay

The MMPs were simultaneously modified with $P1_{rpoB}$ and $P1_{capC}$, to capture targets $T_{rpoB}$ and $T_{capC}$, respectively. The PMPs of 1.04 µm diameter were modified with $P2_{rpoB}$ and pagA, while the PMPs of 0.97 µm diameter were modified with $P2_{capC}$ and pagA. Briefly, a 3.5 µl suspension of MMPs (10 mg ml$^{-1}$) was mixed with 2.5 µg $P1_{rpoB}$ and 2.5 µg $P1_{capC}$. A 3.5 µl suspension of 1.04 µm diameter PMPs (10 mg ml$^{-1}$) was mixed with 2.5 µg $P2_{rpoB}$ and 2.5 µg pagA. Similarly, a 3.5 µl suspension of 0.97 µm diameter PMPs (10 mg ml$^{-1}$) was mixed with 2.5 µg $P2_{capC}$ and 2.5 µg pagA. These mixtures were incubated for 30 min at room temperature with gentle shaking and the MMPs and two types of modified PMPs were then rinsed with 200 µl of wash buffer, three times, to remove the residual oligonucleotides. For each washing step, the MMPs were collected using a magnetic separation rack, while the PMPs were collected by centrifugation (13.8 g for 5 min). Next, 1500 µl of hybridization buffer with different types of target oligonucleotides (a blank sample containing only a buffer solution, $T_{rpoB}$, $T_{capC}$ or $T_{rpoB}$+$T_{capC}$) at 50 pM was first mixed with the MMPs and incubated for 30 min at room temperature with gentle shaking. The MMPs were then separated from the suspension using a magnetic separation rack. Subsequently, the suspension of two types of modified PMPs was mixed with the MMPs in 20 µl of hybridization buffer and the mixture was incubated for 30 min at room temperature with gentle shaking. Finally, a magnetic separation rack or a magnet was used to provide magnetic attraction removing the MMPs and MMPs-targets-PMPs from the suspension, and the solution turbidity was quantitatively analyzed using a UV-Vis spectrometer.

Figure 5:
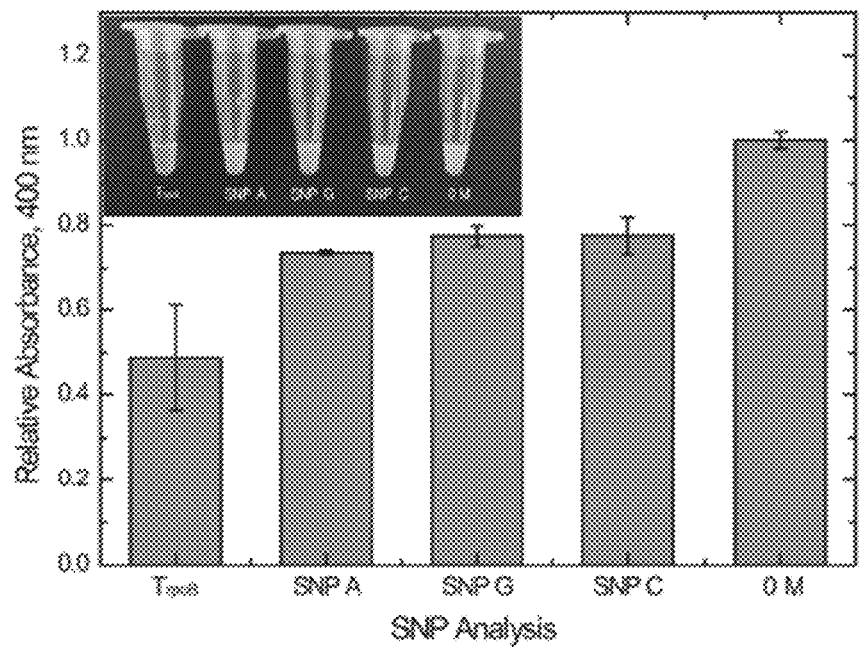
FIG. 5 shows a single nucleotide polymorphism (SNP) analysis with optical images and relative UV-Vis spectral absorbance of the suspensions resulting from 5 nM of $T_{rpoB}$, SNP A, SNP G or SNP C, at 400 nm. For SNP A, SNP G and SNP C the eighth nucleotide, T, of $T_{rpoB}$ was replaced by A, G or C, respectively. The absorbance of the suspension resulting from the blank sample (hybridization buffer with 0 M target nucleic acid sequence) was used as the reference. The relative absorbance is from repeated experiments (mean±SEM, n=3).

The specificity of this method was analyzed by using single nucleotide polymorphisms (SNPs). SNP A, SNP G and SNP C designed based on the target oligonucleotides $T_{rpoB}$ but with the eighth nucleotide, T, replaced by A, G or C. The results showed that although the relative absorbance for the solutions of SNP A, SNP G and SNP C was slightly lower compared to the blank sample (hybridization buffer with 0 M of the target), they were significantly different from that of $T_{rpoB}$ (FIG. 5), indicating their ability to differentiate target oligonucleotides with single nucleotide mismatched sequences.

Figure 9:
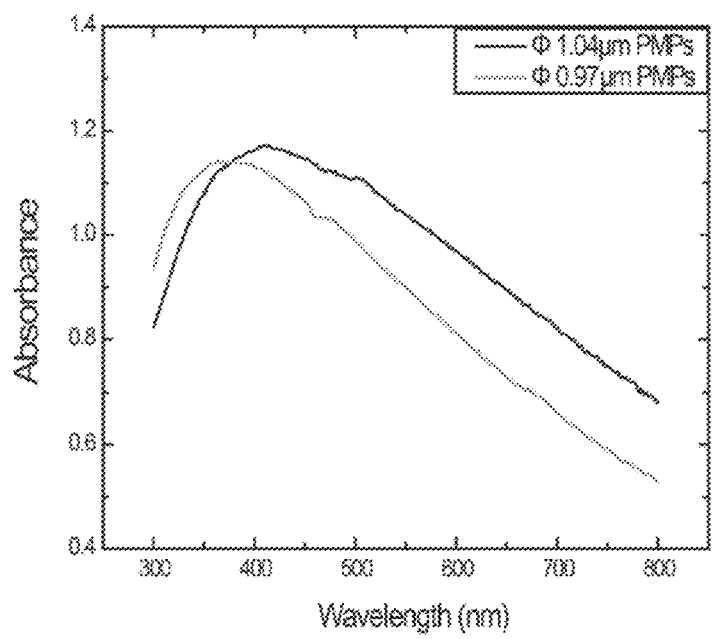
FIG. 9 shows UV-Vis spectral absorbance of the solution of PMPs with 0.97 μm-diameter and 1.04 μm-diameter.

A second type of PMP with 0.97 µm diameter was introduced to detect $T_{capC}$. As PMPs differ in size, the spectrum of absorbance in the suspension of PMPs showed a red shift (FIG. 9), providing signal characters for multiplex assays. 0.97 µm diameter PMPs modified with $P2_{capC}$ and pagA were used to detect $T_{capC}$ and the 1.04 µm diameter PMPs modified with $P2_{rpoB}$ and pagA were used to detect $T_{rpoB}$.

Figure 6:
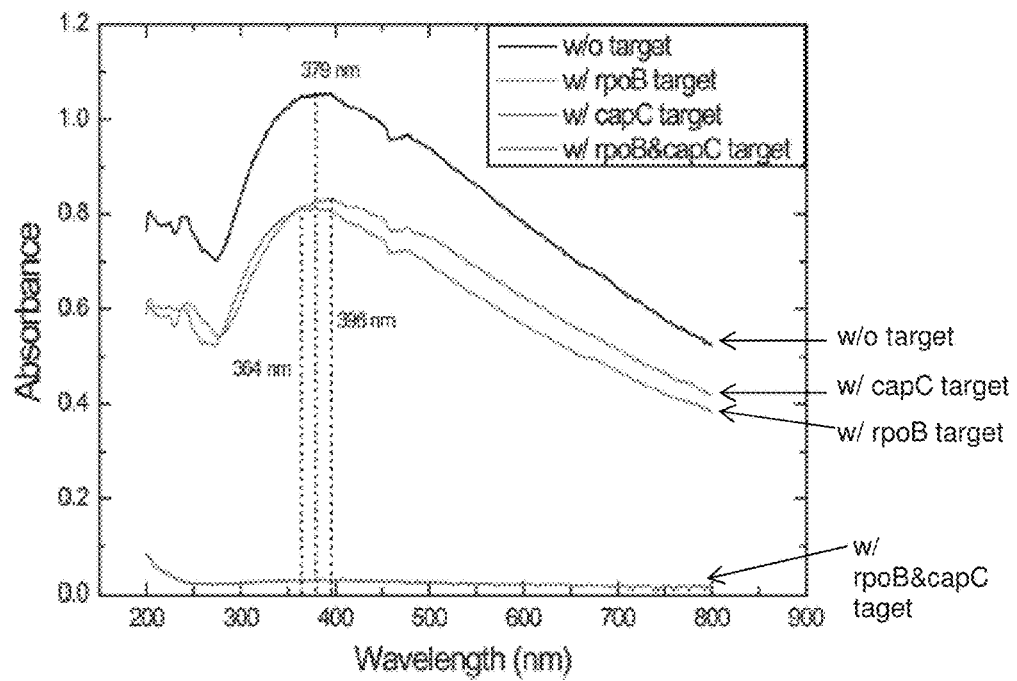
FIG. 6 shows a multiplex detection of $T_{rpoB}$ and $T_{capC}$ conducted with MMPs loaded with $P1_{rpoB}$+$P1_{capC}$, 0.97 μm-diameter PMPs loaded with $P2_{capC}$+pagA for detecting $T_{capC}$, and 1.04 μm-diameter PMPs loaded with $P2_{rpoB}$+pagA for detecting $T_{rpoB}$, the spectral absorbance showed a peak at 379 nm when the target nucleic acid sequence was absent; it shifted to 364 nm when exposed to $T_{rpoB}$ solution at 50 pM, and to 396 nm when exposed to $T_{capC}$ solution at 50 pM. When exposed to both $T_{rpoB}$ and $T_{capC}$, the solution became transparent.

The MMPs were simultaneously modified with $P1_{capC}$ and $P1_{rpoB}$. Before exposure to $T_{rpoB}$ or $T_{capC}$, the mixed particle suspension showed an absorbance peak near 379 nm (FIG. 6). However, when the solution of $T_{rpoB}$ at 50 pM was mixed with the particles, after incubation, magnetic attraction only pulled the 1.04 µm diameter PMPs to the sidewall, leaving the 0.97 µm diameter PMPs suspended and the absorbance peak shifted from 379 nm to 364 nm. In contrast, for the solution containing only $T_{capC}$, only the 0.97 µm diameter PMPs were magnetically attracted, shifting the absorbance peak to 396 nm. In addition, when both $T_{rpoB}$ and $T_{capC}$ were present, both kinds of PMPs were attracted to the sidewall, resulting in a transparent suspension with nearly zero absorbance. Thus, these tests demonstrate that the PMP-based magnetophoretic assay as described herein is capable of multiplex detection of target oligonucleotides at concentrations as low as 50 pM.

Detection in a Complex Bio-Fluid Environment

MDA-MB-231 human mammary gland metastatic epithelial cells (ATCC, USA) were cultured in Dulbecco's Modified Eagle Medium/Nutrient Mixture F-12 (DMEM/F-12) supplemented with 10% fetal bovine serum and 1% penicillin-streptomycin (PS). The cells were incubated at 37° C. in humidified incubator (5% $CO_2$ and 95% air) and passaged every 3 days.

6000 or less cells was added with 1 ml of trizol for 5 min at room temperature, followed by adding 0.2 ml of chloroform and vortex for 15 sec. After incubation on ice for 10 min, the solution was centrifuged at 13.8×g at 4° C. for 15 min, followed by transferring the aqueous phase to a new tube. The aqueous phase solution was then added with 0.5 ml of isopropyl alcohol with gentle vortex and incubated for 10 min. After centrifugation at 13.8×g at 4° C. for 15 min and removing the supernatant, 1 ml of ethanol was added to rinse the RNAs. Next, the sample was centrifuged at 13.8×g at 4° C. for 5 min to remove the ethanol and the pellet was left dried after ethanol evaporation. Finally, DEPC-treated water was used to re-suspend the RNAs by incubation at 65° C. The total RNA was then stored at −80° C. until use. For the detection, the solution was prepared by 100 pM $T_{rpoB}$ mixed with 641 ng/ml RNAs in hybridization buffer, and the final volume was brought to 1500 μl.

MMPs and PMPs modified with probes recognizing $T_{rpoB}$ were prepared as described. 1500 μl of rabbit whole blood (Qiyi Biological Technology Co., Ltd) or a solution of nucleic acid pool isolated from human mammary gland metastatic epithelial cells (MDA-MB-231) with varying concentrations of the target $T_{rpoB}$, was mixed with 35 μg of MMPs and incubated for 30 min at room temperature with gentle shaking. The MMPs were then collected from the bio-fluid using a magnetic separation rack and rinsed in 1500 μl of wash buffer, three times, to remove the residual rabbit blood. This step removed the target $T_{rpoB}$ from the interference of the bio-fluid environment. Afterwards, the MMPs were mixed with 35 μg of modified PMPs in 20 μl of hybridization buffer and incubated for 30 min at room temperature with gentle shaking.

A magnetic separation rack or a magnet was used for magnetic attraction, and the solution turbidity was observed directly by the naked eye or quantified using a UV-VIS spectrometer.

Figure 7A:
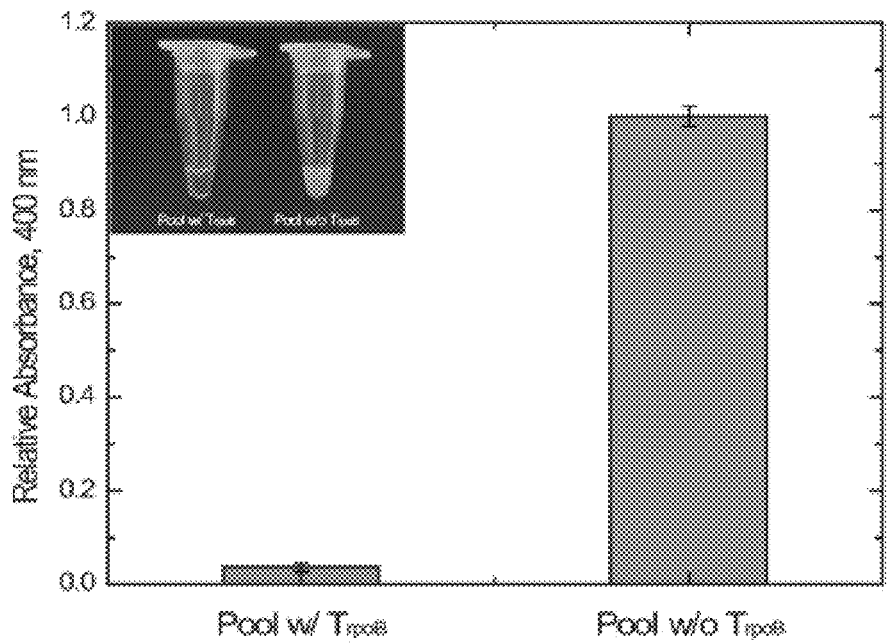
FIGS. 7A and 7B show the detection in a complex bio-fluid environment.

Compared to AuNPs, one of the advantages of using PMPs proved to be the stability of the particle suspension and the tolerance to interfering biomolecules. The detection was made under the interference from a pool of nucleic acids isolated from human mammary gland metastatic epithelial cells (MDA-MB-231). $T_{rpoB}$ was extracted with MMPs, followed by washing steps to remove the residual bio-fluid via magnetic separation. The MMPs with extracted $T_{rpoB}$ were then mixed with the PMPs for the magnetophoretic assay. One hundred pM of $T_{rpoB}$ was mixed with 641 ng ml$^{-1}$ RNAs extracted from the cell lysate. The results showed that the presence of interfering molecules does not hinder the detection (FIG. 7A).

Figure 7B:
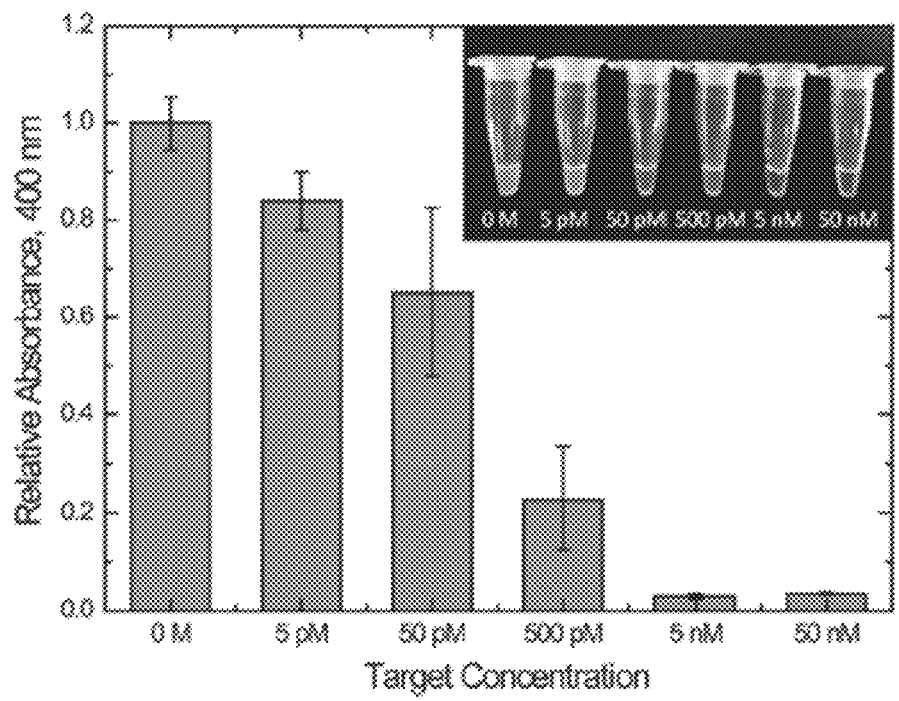

Furthermore, to demonstrate the compatibility with the whole blood environment, the target molecule $T_{rpoB}$ was mixed in undiluted rabbit blood at concentrations of 0 M, 5 pM, 50 pM, 500 pM, 5 nM and 50 nM. The results showed that, although the total absorbance was reduced, possibly caused by non-specific binding of the complex components of blood, a limit of detection as low as 50 pM by visual inspection and 5 pM by UV-Vis spectral analysis were achieved (FIG. 7B).

Altogether, these results demonstrated that the method of the present invention is compatible with complex biofluids, and retains its high sensitivity without the need for additional purification processes, indicating its potential for future practical applications such as on-site examination.

Determination of the Extinction Coefficient of the Resultant PMP Suspension

The enhanced extinction coefficient due to the Mie scattering by PMPs provides a limit of detection lower than, or comparable to, the AuNP-based method (50 pM). The Mie scattering describes a phenomenon where an electromagnetic plane wave passes by homogeneous spheres, the size of which is comparable to the wavelength of light. When a light beam passes a solution, the intensities of the incident and scattered light together with the absorbed beam follow Lambert-Beer's law:

$$A_\lambda = \varepsilon c L$$

where $A_\lambda = \ln(I_i/I_o)$ is the spectral absorbance at the wavelength λ, $I_i$ is the intensity of the incident beam, $I_o$ is the intensity of the beam passing through the solution, ε is the extinction coefficient, c is the concentration of PMPs in the suspension and L is the pathlength of light. The extinction coefficient ε for spheres is a function of size parameter πd/λ. When the diameter d is 600-1200 nm, λ=546.1 nm and the refractive index n=1.333, E reaches a high value range of specific turbidity.

Based on the measurement using a UV-VIS spectrometer at 400 nm for a series dilution of PMP suspension, the extinction coefficient ε was calculated as $4.457×10^{12}$ M$^{-1}$ cm$^{-1}$ (FIG. 8), which is 3 orders of magnitude greater than that of AuNPs (typically at the scale of $10^9$ M$^{-1}$ cm$^{-1}$ for a diameter of 20-40 nm). Thus, although larger PMPs may need more targets to form the particle-particle connection, the significantly enhanced extinction coefficient compensates this shortcoming, making the method as sensitive as that of AuNP-based assays.

Discussion on SNP analysis

For the SNP analysis, the hybridization energy between SNP A, G, or C and $P1_{rpoB}$ is −12.02 kcal mol$^{-1}$, which is much greater than the hybridization energy, −25.07 kcal mol$^{-1}$, between $T_{rpoB}$ and $P1_{rpoB}$. Accordingly, the single base mismatch leads to a significant decrease of the binding strength between MMPs and PMPs. For the PMP-based magnetophoretic assay, the flow of PMPs was driven by the movement of MMPs but also resisted by the friction following Stokes' law, $F=6\pi\mu rV$, where μ is the dynamic viscosity, r is the radius of microparticles, and V is the particle velocity. For PMPs with a diameter of 1.04 μm, this friction is significantly larger than that of the commonly used nanoparticles (~2 orders of magnitude greater). Thus, the weaker connections due to SNP A, G or C were more vulnerable during magnetophoretic flow, which would lead to the differentiation of perfect matched or single mismatched targets.

Example 2

Figure 11:
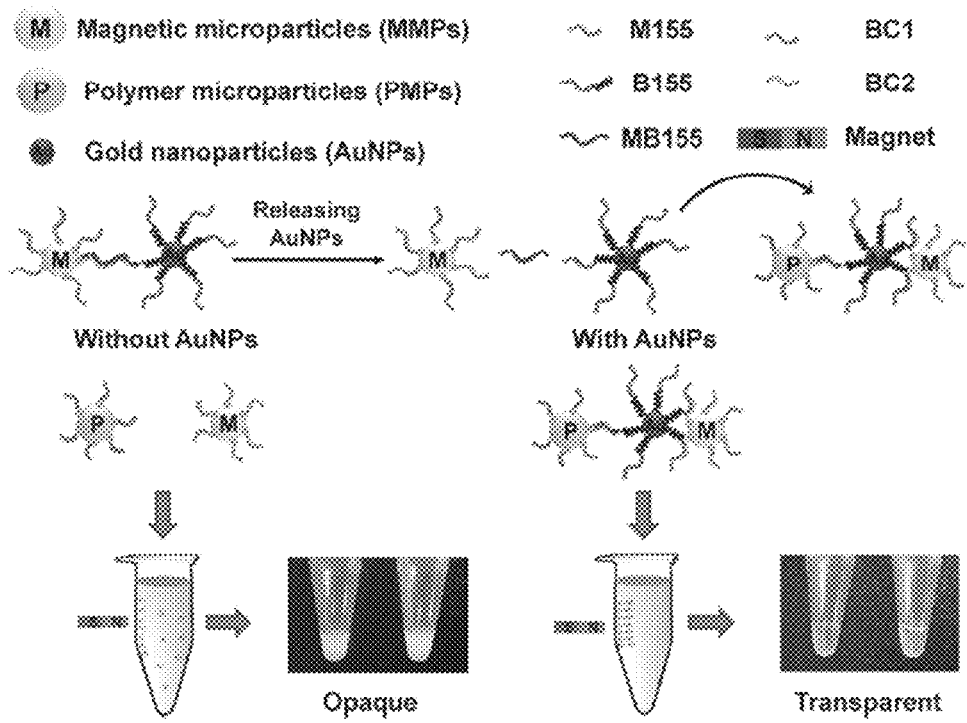
FIG. 11 is a schematic diagram showing the operating principle of the method of the present invention, in particular with a gold particle being applied.

Method of determining the presence or amount of a target nucleic acid sequence by using a magnetic particle, a polystyrene particle and a gold particle FIG. 11 demonstrates an example of the present invention. For the target nucleic acid sequence MB155, it is a sequence the same as that of a type of microRNA, miR-155, that is highly expressed in breast cancer cells.

The method first employs a first magnetic particle loaded with a first probe, M155, and a gold nanoparticle loaded with a second probe, B155, to bind to the target nucleic acid sequence MB155 in the sample. The first probe M155 and the second probe B155 are complementary to the target nucleic acid sequence MB155. After hybridization and isolation, the first complex having the target nucleic acid sequence bound to the first magnetic particle and the gold nanoparticle is obtained.

The gold nanoparticle loaded with the second probe is then released from the first complex and is subjected to a mixture containing another type of magnetic particle, i.e. a second magnetic particle loaded with a third probe BC2, and a polystyrene particle loaded with a fourth probe BC1. The third probe BC2 and fourth probe BC1 are complementary to the second probe B155.

The released gold nanoparticle contains hundreds of B155 oligonucleotides with sequence complementary to the sequence of BC1 and BC2 and acts as the sticky balls that can link second magnetic particle and the polystyrene particle together by hybridization in juxtaposition. Accordingly, a second complex having the second probe on the gold nanoparticle bound to the second magnetic particle and the polystyrene particle, i.e. MMP-AuNP-PMP, is obtained.

After applying the magnetic field, the complex MMPs-AuNPs-PMPs could be moved to the sidewall, yielding a change of solution turbidity from opaque to transparent due to the reduction of suspended PMPs. Since PMPs are large (1.04 μm in diameter), the change of turbidity is caused by Mie scattering that can effectively attenuate light transmission with significantly enhanced extinction coefficient, i.e. around 3 orders of magnitude greater than that of commonly used gold nanoparticles.

Moreover, as the AuNPs are in nano-scale, only very small amount of target oligonucleotides was required for the collection of AuNPs in the first process. Therefore, the few target nucleotides were exchanged to AuNPs modified with many oligonucleotide probes, which were used for the connection between MMPs and PMPs with significantly enhanced binding strength that amplified the signals.

It is found that using this enzyme-free amplification, the LOD reached 10 amol for ssDNAs (228 fM in 45 μL) and 75 amol for ssRNAs (1.67 pM in 45 μL). This method is also applicable for detection of the target oligonucleotides in the blood serum and microRNAs, miR-155, extracted from human mammary gland metastatic epithelial cells (MDA-MB-231 cell line).

In addition, comparing total analysis time among different known amplifications, this method requires only 3 h, which is comparable with the requirements of enzymatic methods (2 h and 40 min), DNA circuits (4 h), and biobarcode assay (3-4 h). With similar total analysis time, this method does not require enzymatic reaction or additional chemical reaction to dissociate biobarcode oligonucleotides and is compatible with the blood serum or detection of microRNAs extracted from cell lysates.

Materials and Reagents

The single strand oligonucleotides, tris(2-carboxyethyl) phosphine (TCEP), and sodium dodecyl sulfate (SDS) were purchased from Sangon Biotech Ltd. The tris-ethylenediaminetetraacetic acid (Tris-EDTA) buffer, potassium phosphate, Tris-HCl, EDTA, Trition X-100, and NaCl were obtained from Sigma-Aldrich. The blood serum was fetal bovine serum from Life Technology. The MMPs of 0.90 μm in diameter (CM01N, Bangs Laboratories, Inc., USA) and PMPs of 1.04 μm in diameter (polystyrene basis, CP01F, Bangs Laboratories, Inc., USA) were functionalized with a streptavidin coating by the manufacturer using covalent conjugation with a zero-length cross-linker. The AuNPs with a diameter of 30 nm were purchased from PERSer Nanotechnology, Ltd. All chemicals were of analytical grade. Deionized (DI) water with a resistivity of 18.2 MΩ cm was obtained from a Milli-Q Plus system.

Oligonucleotide Sequences

The single strand oligonucleotides were dissolved in Tris-EDTA buffer. These sequences are listed in Table 2. The oligonucleotide probes M155 and B155 were designed with sequences partially complementarity to the target oligonucleotide MB155 in juxtaposition, and oligonucleotide probes BC1 and BC2 were designed with sequence partially complementarity to the oligonucleotide B155 in juxtaposition. The oligonucleotide B155 was functionalized with (PEG) 6-thiol at its 3' end, which avoids steric hindrance during hybridization between BC2 and B155. Bi155 was designed on the basis of B155, but the (PEG) 6-thiol at its 3' end was replaced by biotin. MBr155 is the RNA-based oligonucleotide designed accordingly to the sequence of MB155. SNP A, SNP T, and SNP C were designed with a single-base mismatch (shown in bold underlined italic) compared to MB155.

TABLE 2

The sequences of the single-strand oligonucleotides

| Strand name | Comprises SEQ ID NO. | Structure of the sequence |
| --- | --- | --- |
| M155 | 13 | 5'-/biotin/-CCCCTATCACG-3' |
| B155 | 14 | 5'-ATTAGCATTAAACTCGGATCACTCG-(PEG)6- thiol-3' |
| Bi155 | 15 | 5'-ATTAGCATTAA-/biotin/-3' |
| MB155 | 16 | 5'-TTAATGCTAATCGTGATAGGGG-3' |
| MBr155 | 17 | 5'-UUAAUGCUAAUCGUGAUAGGGG-3' |
| SNP A | 18 | 5'-TTAAT_A_CTAATCGTGATAGGGG-3' |
| SNP T | 19 | 5'-TTAAT_T_CTAATCGTGATAGGGG-3' |
| SNP C | 20 | 5'-TTAAT_C_CTAATCGTGATAGGGG-3' |
| BC1 | 21 | 5'-GTTTAATGCTAAT-/biotin/-3' |
| BC2 | 22 | 5'-/biotin/-CGAGTGATCCGA-3' |

Modification of Gold Nanoparticles (PEG) 6-thiol-functionalized probe B155 (100 μM, 25 μL) was first activated by 5 equiv. of TCEP for 1 h. Then, the TCEP-activated B155 was added to 1 mL of gold nanoparticles (30 nm, 300 pM) at room temperature. After 16 h, 0.01% SDS was added to the solution, and it was brought to a final concentration of 1.0 M NaCl through a stepwise process. Upon aging for 40 h, the AuNPs were isolated by centrifugation 13.8×g for 10 min, washed three times with hybridization buffer (pH 7.4, 10 mM phosphate, 0.3 M NaCl, 0.01% SDS), dispersed in the hybridization buffer, and finally stored at 4° C. until use. To estimate the number of oligonucleotides loaded on the AuNPs, FAM-labeled DNAs to modify AuNPs was used.

The FAM-labeled DNAs were later dissociated by mixing with an equal volume of 1.0M DTT in 0.18 M PBS buffer (pH 8.0) for incubation overnight. After removing AuNPs by centrifugation, the fluorescence of the solution was measured and compared to a standard curve of the fluorescence intensity and FAM concentration. It is found that there were approximately 330 oligonucleotides loaded on each AuNP, which was equal to $2.919 \times 10^{12}/cm^2$.

Modification of Magnetic Microparticles and Polystyrene Microparticles

The oligonucleotide probes (M155, Bi155, BC1, and BC2) were biotinylated so that they can spontaneously attach to streptavidin-coated MMPs and PMPs. Briefly, 3.5 μL of MMPs or PMPs solution (10 mg/mL; $1.278\times10^{10}$ and $1.617\times10^{10}$ particles/mL for MMPs and PMPs, respectively) was added to the solution containing 2.5 μg of oligonucleotide probes. Each MMP and PMP would allow the attachment of $1.6\times10^6$ and $2.5\times10^5$ oligonucleotide probes, respectively ($6.28\times10^8/cm^2$ on MMPs and $4.32\times10^8/cm^2$ on PMPs).

2.5 μg of oligonucleotide probes were mixed with 35 μg of MMPs or PMPs, which is equal to $3.5\times10^6$ and $5.4\times10^5$ oligonucleotide probes for each MMP and PMP, respectively. Thus, the provided number of oligonucleotide probes is significantly greater than the total capacity of microparticles, which ensures that all binding sites were fully loaded.

The mixture was incubated for 30 min at room temperature with gentle shaking to allow the immobilization of biotinylated oligonucleotides on streptavidin-coated microparticles. Next, the MMPs and PMPs were rinsed three times with 200 μL of wash buffer (20 mM Tris-HCl, pH 7.5, 1 M NaCl, 1 mM EDTA, 0.0005% Triton X-100) to remove residual oligonucleotides. For each washing step, the MMPs were collected using a magnetic separation rack, whereas the PMPs were collected using a centrifuge (13.8×g for 5 min). At the end, the MMPs and PMPs were suspended in hybridization buffer with the final concentration 10 mg/mL.

Hybridization of Magnetic Microparticles and Gold Nanoparticles with Target Oligonucleotides For the detection of oligonucleotide, 1 μL of control sample containing pure hybridization buffer, target oligonucleotide solution with varying concentration prepared in hybridization buffer, or target oligonucleotides with single-base mismatch at 250 pM in hybridization buffer was added to 3.5 μL of MMPs (10 mg/mL) modified with M155 probes. For MBr155, RNAase inhibitor at 1 U/μL was supplemented. Hybridization was conducted for 30 min with gentle vortexing at room temperature. Then, 40.5 μL of B155-modified AuNPs was added to the mixed solution, hybridization was allowed with gentle vortexing for 30 min, and the final volume became 45 μL.

Hybridization of Magnetic Microparticles and Gold Nanoparticles with Target Oligonucleotides in Blood Serum Pure blood serum (1 μL of control sample) or blood serum containing varying concentration of target oligonucleotides MB155 was added to 3.5 μL of MMPs (10 mg/mL) modified with M155 and hybridization was allowed for 30 min with gentle vortexing at room temperature. Then, the MMPs with target oligonucleotides were collected by magnetic field. After rinsing the MMPs three times to remove the residue from blood serum, 4.5 μL of hybridization buffer was added. Next, 40.5 μL of B155-modified AuNPs were added allowed to hybridize with gentle vortexing for 30 min, and the final volume was left as 45 μL.

Collection of Bound Gold Nanoparticles

After hybridization, the MMPs-targets-AuNPs could be attracted to the sidewall by applying the magnetic field for 2 min, and the unbound AuNPs were removed. Next, the MMPs-targets-AuNPs were resuspended in 5 μL of DI water and heated at 70° C. for 5 min to release the AuNPs. The thiol-gold bond can remain stable in this heating step. Finally, the salt concentration of the released-AuNPs solution was adjusted by adding 5 μL of 2× hybridization buffer (pH 7.4, 20 mM phosphate, 0.6 M NaCl, 0.02% SDS), and the final volume was 10 μL.

Visual Detection of MMPs-AuNPs-PMPs

To the solution of released AuNPs was then added 3.5 μL of BC2-modified MMPs (10 mg/ml), and hybridization was conducted with gentle vortexing at room temperature for 60 min. Next, to the mixture was added 3.5 μL of BC1-modified PMPs (10 mg/mL), and hybridization was conducted with gentle vortexing for 60 min at room temperature. The final volume was 17 μL. Finally, a magnetic field was applied for 2 min to attract the unreacted MMPs and MMPs-AuNPs-PMPs to the sidewall so that the solution with PMP suspension can be collected for direct visual inspection or quantitative analysis by UV-VIS spectrometer (BioDrop μLITE, UK).

Figure 12:
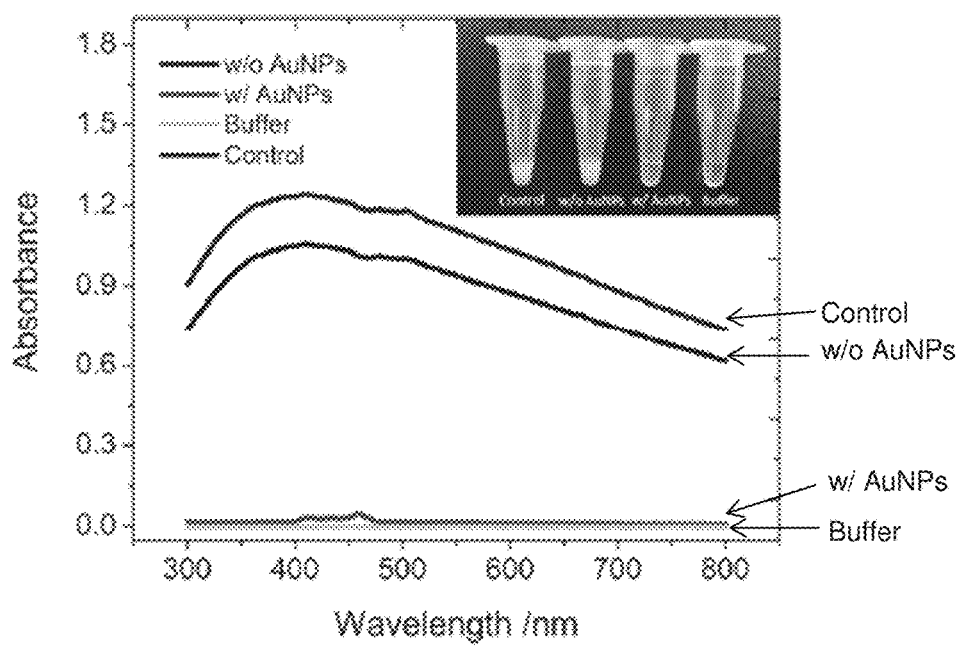
FIG. 12 shows spectral absorbance and (inset) optical images of the solution with PMP suspension resulting from the tests with or without AuNP amplification.

As shown in the FIG. 12, target oligonucleotides at 250 pM was used in the first process, the AuNP amplified magnetophoretic effect caused the solution turbidity to become as transparent as that of the buffer solution. Measured by UV-VIS spectrometer, the spectral absorbance was almost the same. For comparison, another experiment where 1 nM B155 oligonucleotide molecules were directly applied to the mixture of BC2-modified MMPs and BC1-modified PMPs was performed. Without AuNP amplification, the results showed that the solution was almost as opaque as the control sample that only had MMPs and PMPs. The UV-VIS spectrum also showed that the absorbance only decreased little compared to that of control sample. Thus, by using AuNPs as the nano sticky balls for signal amplification, the sensitivity was significantly enhanced.

Cell Culture

MDA-MB-231 human mammary gland metastatic epithelial cells (ATCC, USA) were cultured in Dulbecco's modified Eagle's medium/nutrient mixture F-12 (DMEM/F-12) supplemented with 10% fetal bovine serum and 1% penicillin-streptomycin (PS). MCF-10A human mammary gland epithelial cells (ATCC, USA) were cultured in DMEM/F-12 supplemented with 5% horse serum (HS), 1% PS, 20 ng/mL epidermal growth factor, 0.5 mg/mL hydrocortisone, and 10 ug/mL insulin. For neutralizing the toxicity of trypsin during passaging, a re-suspension medium for MCF-10A cells was prepared using DMEM/F-12 supplemented with 20% HS and 1% PS. All the cell lines were incubated at 37° C. in a humidified incubator (5% CO2 and 95% air) and passaged every 3 days.

Extraction and Detection of MicroRNAs from Cells

Trizol (1 mL) was added to 6 million cells (or fewer) for 5 min at room temperature. Then, 0.2 mL of chloroform was added and vortexed for 15 s. The mixed solution was incubated on ice for 10 min and centrifuged at 13.8×g at 4° C. for 15 min. Next, the upper aqueous phase was transferred to a new tube, and to this was added 0.5 mL of isopropyl alcohol with gentle vortexing, followed by incubation for 10 min. The mixed solution was centrifuged at 13.8×g at 4° C. for 15 min, and the supernatant was removed. After adding 1 mL of ethanol to wash the RNAs gently, the mixture was centrifuged at 13.8×g at 4° C. for 5 min, followed by the removal of the supernatant and drying to make sure all the ethanol had been evaporated. Finally, DEPC-treated water was added, and the mixture was incubated at 65° C. to resuspend the RNAs in a final volume of 7 μL for storage at −80° C. DEPC treated water without RNA (7 μL) was used as the control sample. For detection, the RNA solution was added with PCR buffer (200 mM Tris HCl (pH 8.4), 500 mM KCl, 15 mM MgCl2) to adjust salt concentration and RNAase inhibitor at 1 U/μL, and the final volume was adjusted to 10 μL. The RNA solution was then incubated with 3.5 μL of MMPs solution for 0.5 h, followed by isolation of MMPs and hybridization with AuNPs for subsequent visual detection via the aforementioned procedure.

Quantitative Reverse transcription PCR (qRT-PCR)

Total RNAs was extracted from 0.68 million cells (MDA-MB-231 and MCF-10A) using a commercial kit (12183555, Life Technology), and its concentration was measured via Biodrop (BioDrop μLITE, UK). The RNA solution from both cell types was mixed with reverse transcription (RT) master mix solution (4366596, Life Technology) and RT primer (assay no. 002623 for miR-155 or assay no. 001973 for U6, the endogenous normalizer, 4427975, Life Technologies). The sealed tube was incubated on ice for 5 min, followed by thermal cycles according to the kit protocol. After reverse transcription, the RT product was added to TaqMan Universal Master Mix II (4440038, Life Technology) and TaqMan Assay 20× (4427975, Life Technologies) following the kit protocol. The sealed strips were loaded into the real-time PCR system (Bio-Rad CFX Connect Real-Time System) following the kit protocol. All samples were repeated three times. The qRT-PCR results were analyzed by relative expression of miR-155 in fold changes by ΔΔCT (cycle threshold) method.

Figure 17:
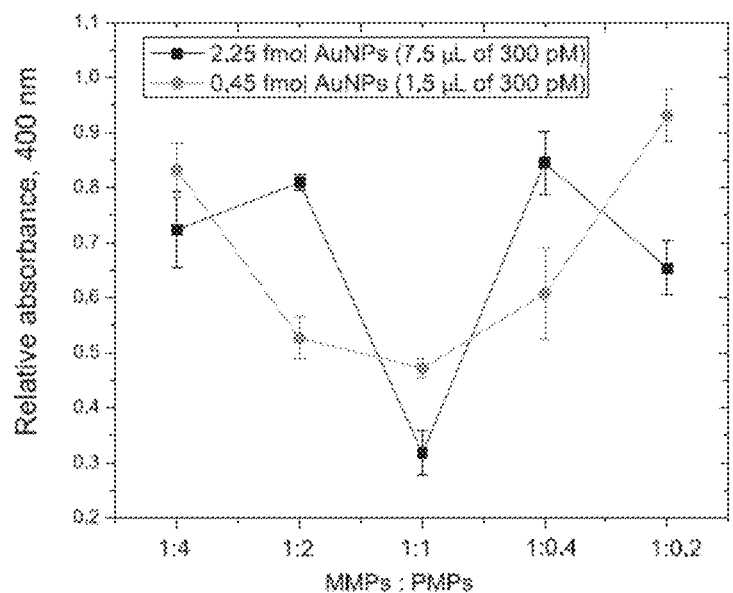
FIG. 17 shows the relative absorbance at 400 nm with optimization of the MMPs:PMPs ratio by varying the MMP concentration.
Figure 18:
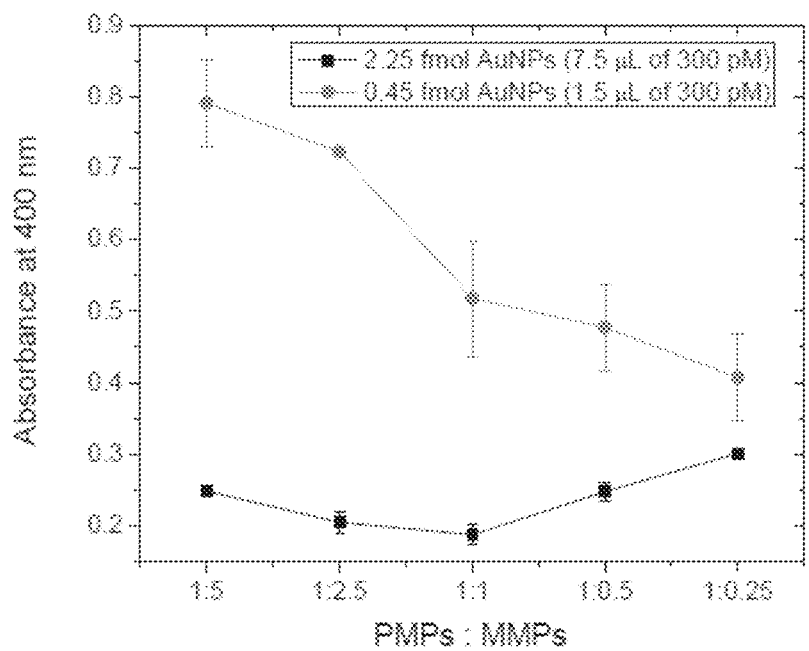
FIG. 18 shows the relative absorbance at 400 nm with optimization of the PMPs:MMPs ratio by varying the MMP concentration.

Optimization of the Applied Ratio of Magnetic Particles to Polystyrene Particles Using 2.25 fmol (7.5 μL at 300 pM) or 0.45 fmol (1.5 μL at 300 pM) of AuNPs modified with B155 to link MMPs with BC2 and PMPs with BC1, the ratio of MMPs and PMPs was varied to obtain the greatest reduction of solution turbidity. By changing the PMP concentration while keeping the MMP concentration intact (35 μg in 17 μL), the most significant reduction of solution turbidity was achieved when the ratio of MMPs and PMPs is 1:1 (FIG. 17). This condition was observed for both high and low concentrations of AuNPs. Alternatively, by changing the MMP concentration only, a similar result was obtained for a high concentration of AuNPs (FIG. 18). The ratio of MMP and PMP was chosen as 1:1 for the optimized combination.

Determination of the Extinction Coefficient

The extinction coefficient was calculated according to the Lambert-Beer Law, where $A_\lambda$ is the spectral absorbance at the wavelength of λ=400 nm, ε is extinction coefficient, and L is the path length of light, 0.05 cm.

The concentration c of the stock solution of PMPs was calculated on the basis of the number concentration provided by the manufacturer ($1.617 \times 10^{10}$ particles/mL, which is equal to $2.686 \times 10^{-11}$ M). On the basis of the measured absorbance for a serial dilution of PMP suspension, the extinction coefficient E was calculated as $4.457 \times 10^{12}$ M$^{-1}$ cm$^{-1}$.

Compared to AuNPs, which are commonly used in many types of visual detection and have an extinction coefficient at the scale of $10^9$ M$^{-1}$ cm$^{-1}$ for a diameter of 20-40 nm, the extinction coefficient of PMPs using Mie scattering is 3 orders of magnitude greater. Thus, the improved sensitivity in this method can be attributed to the significantly enhanced binding strength of nano sticky balls as well as the increased extinction coefficient by Mie scattering.

Determination of the Limit of Detection

Figure 13A:
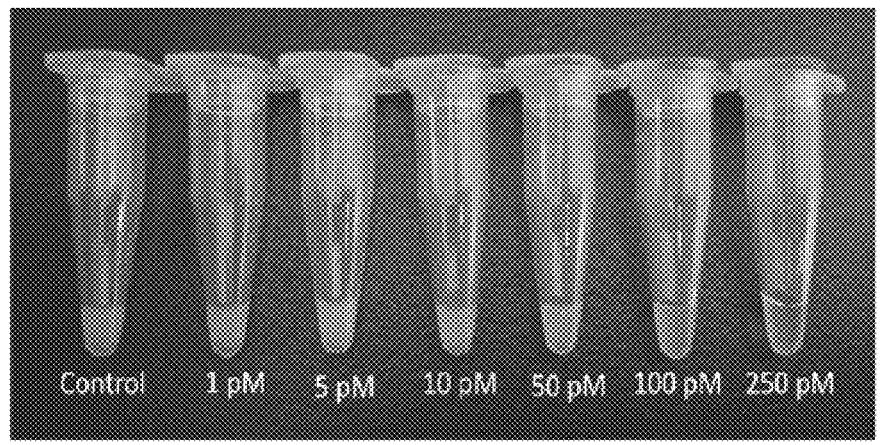
FIGS. 13A, 13B, 13C, 13D, 13E, and 13F show the detection of target ssDNA/RNA oligonucleotides with varying concentrations, namely 0 M, 1 pM, 5 pM, 10 pM, 50 pM, 100 pM, and 250 pM in 45 μL.
Figure 13B:
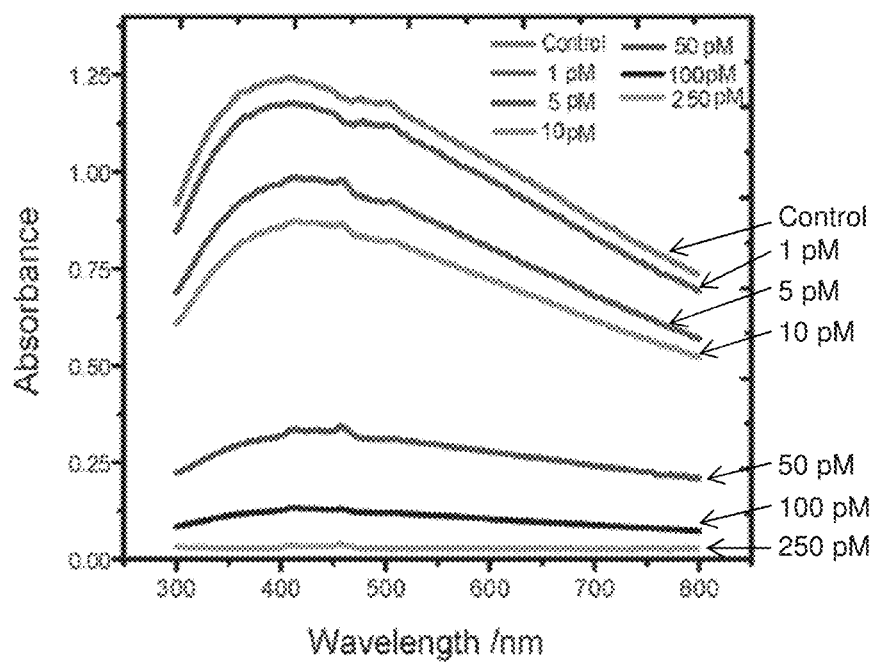
Figure 13C:
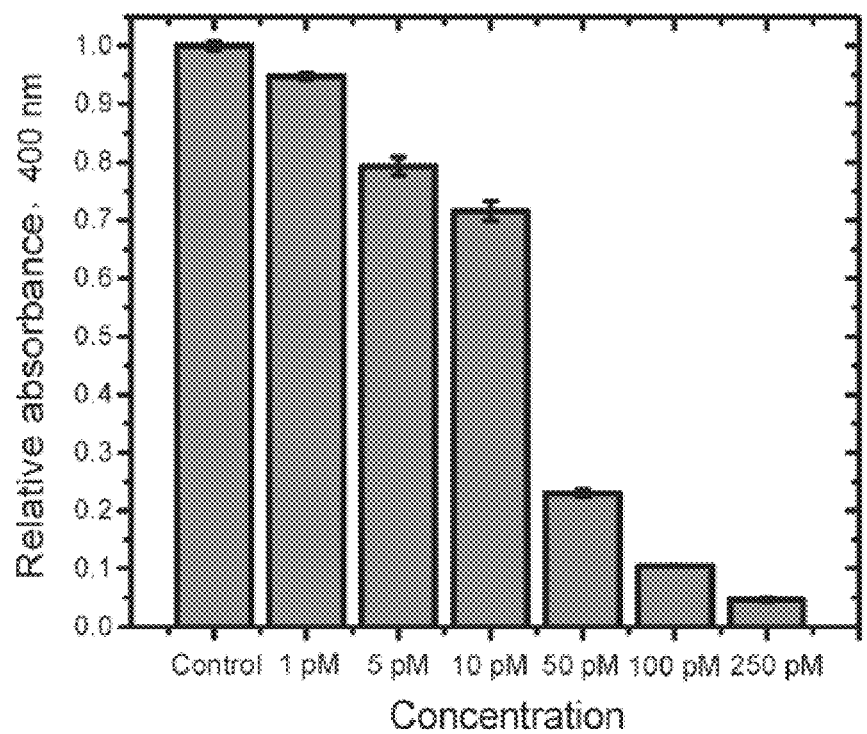
Figure 13D:
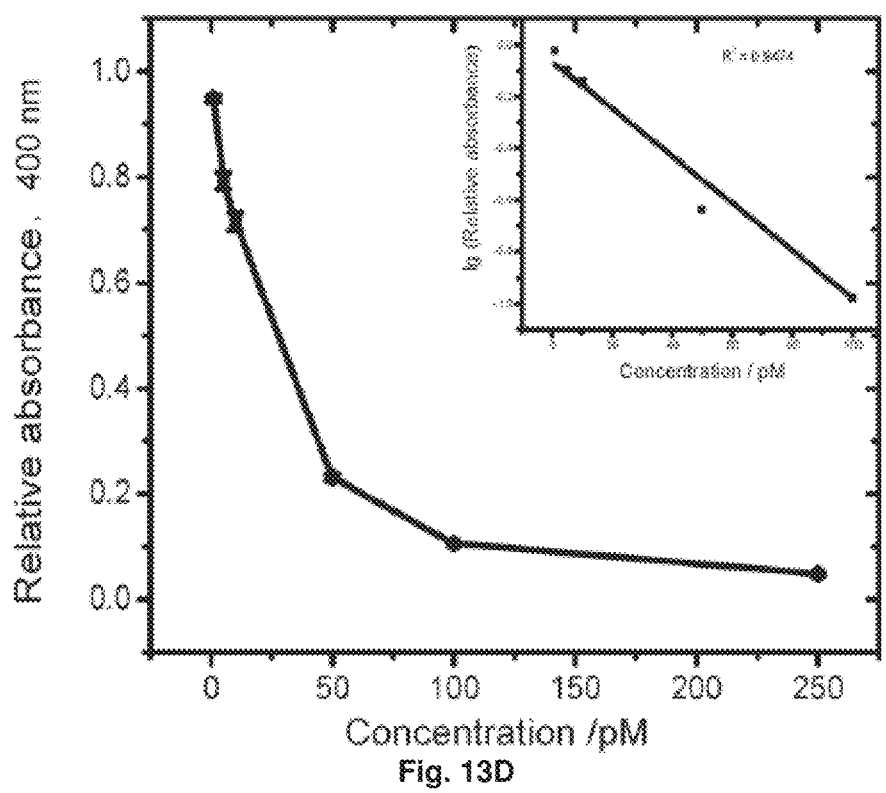

As shown in FIG. 13A, with the use of different concentrations of target oligonucleotide MB155 ranging from 1 pM to 250 pM, the solution turbidity gradually changed from opaque to transparent. Thus, the LOD was 2.25 fmol (50 pM in 45 μL) as determined by the naked eye. In addition, measured by spectral absorbance (FIGS. 13B and 13C), the calibration graph was linear in the range of 1-100 pM (FIG. 13D), with calibration equation determined as $\lg(RA)=-0.00968 C_{MB155}-0.05498$, where RA is the relative absorbance at 400 nm, CMB155 is the concentration of MB155, and the corresponding correlation coefficient ($R^2$) of the calibration curve is 0.9474.

On the basis of the calibration graph, the LOD was 10 amol (228 fM in 45 μL, calculated on the basis of 3σ/m, where a is the standard deviation of the lg(RA) of control sample, and m is the absolute slope of the calibration equation), which is much better than that of other types of visual assays such as AuNP aggregation with DNA circuit or lateral flow strip. Notably, the target MB155 is a DNA oligonucleotide.

Figure 13E:
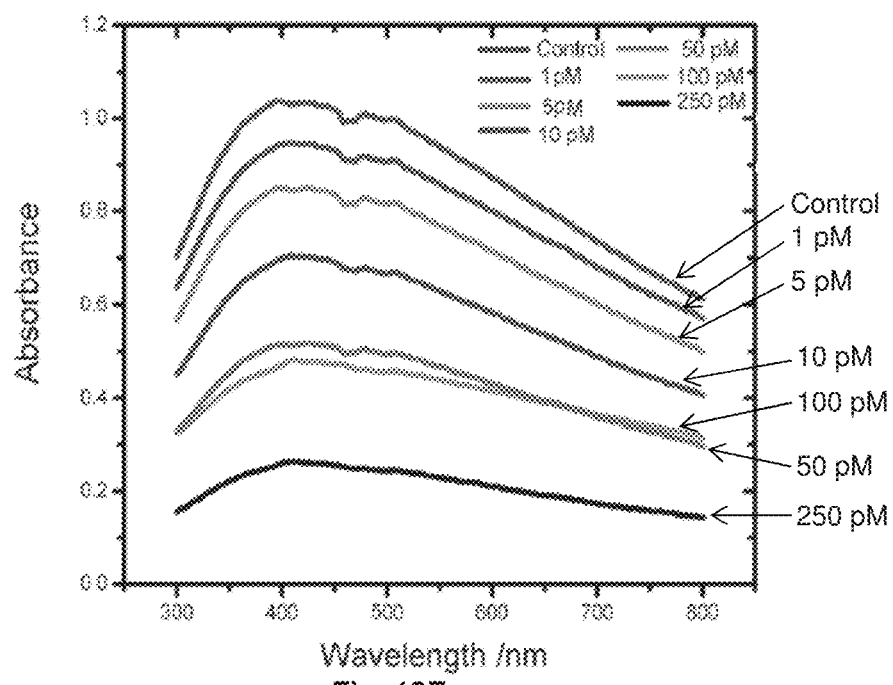
Figure 13F:
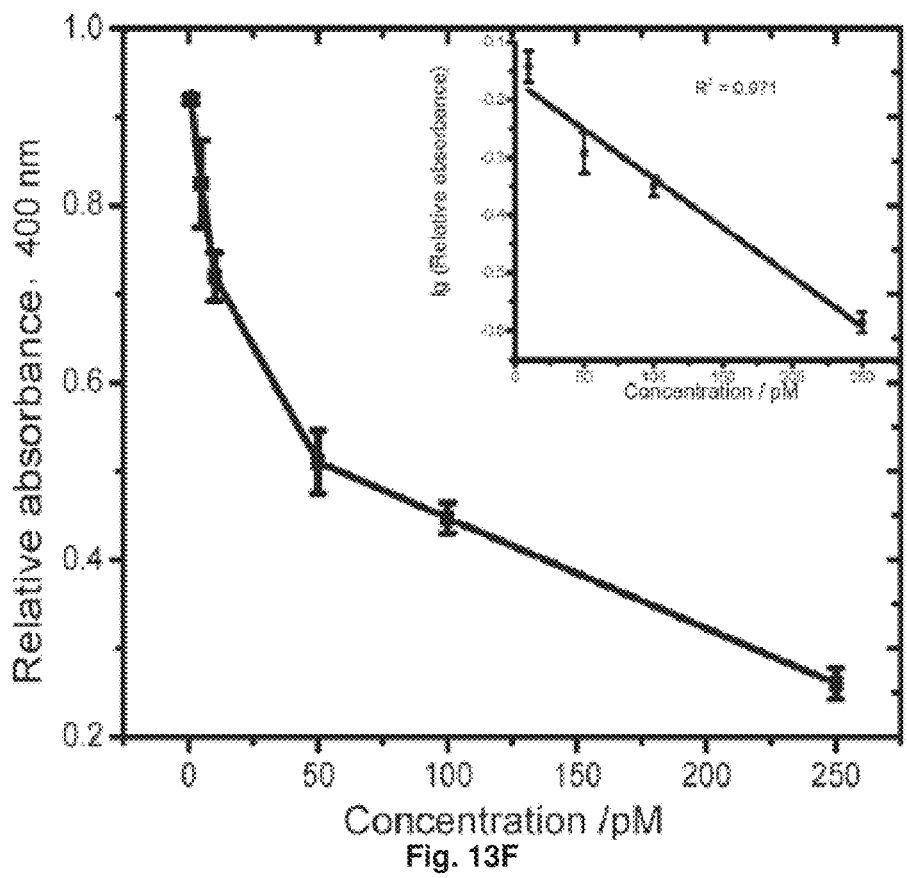

Because short RNA oligonucleotides are extremely degradable, it may not be compatible with the operation principle and may be damaged during the detection procedure, even in well-defined buffer solution. To demonstrate the compatibility of RNAs, MBr155 was used, which is an RNA-based oligonucleotide designed according to the sequence of target DNA MB155. Measured by spectral absorbance (FIG. 13E), the calibration graph was linear in the range of 1-250 pM (FIG. 13F). The calibration equation was determined as $\lg(RA)=-0.0017 C_{MBr155}-0.16673$, where RA is the relative absorbance at 400 nm, $C_{MBr155}$ is the concentration of MBr155, and the corresponding correlation coefficient ($R^2$) of the calibration curve is 0.971. On the basis of the calibration graph, the LOD was 75 amol for ssRNAs (1.67 pM in 45 μL, calculated on the basis of 3σ/m). The result showed that a low level of LOD is achievable, validating the compatibility and practicability of both DNA and RNA nucleic acid sequence determination.

Determination of the Amplification Rate

The amplification rate was determined by comparing the signal with/without

Figure 19:
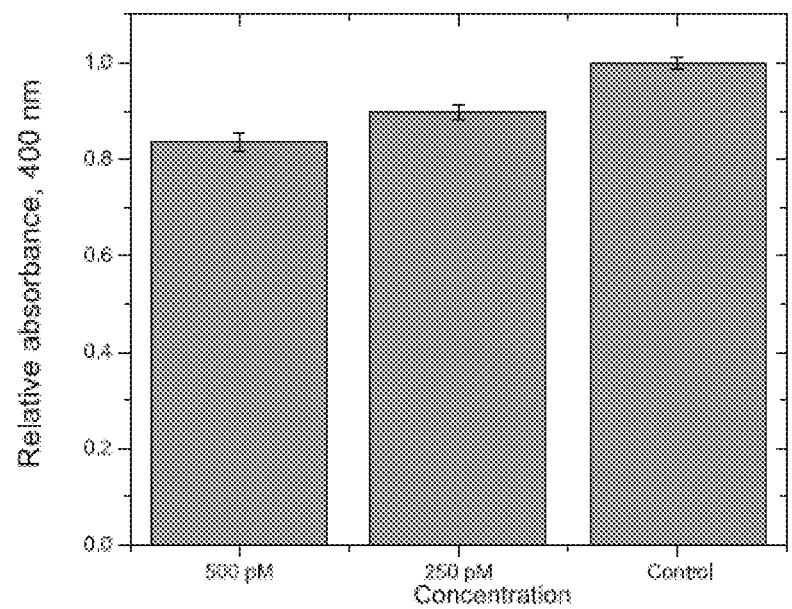
FIG. 19 shows the detection without AuNP amplification. The relative absorbance was measured at 400 nm by repeated experiments (mean±max deviation, n=3). The absorbance of the solution with PMP suspension resulting from the control sample (0 M of MB155) was used as the reference.
Figure 20:
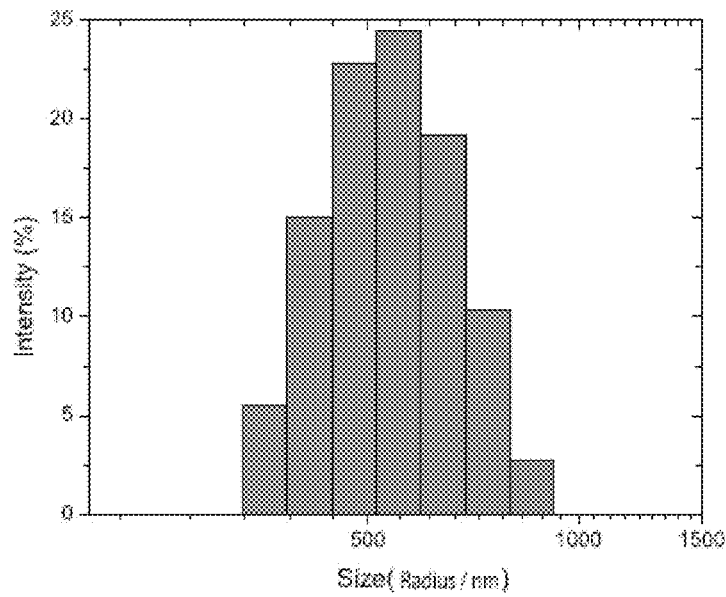
FIG. 20 shows the size distribution of PMPs measured by dynamic light scattering.
Figure 21:
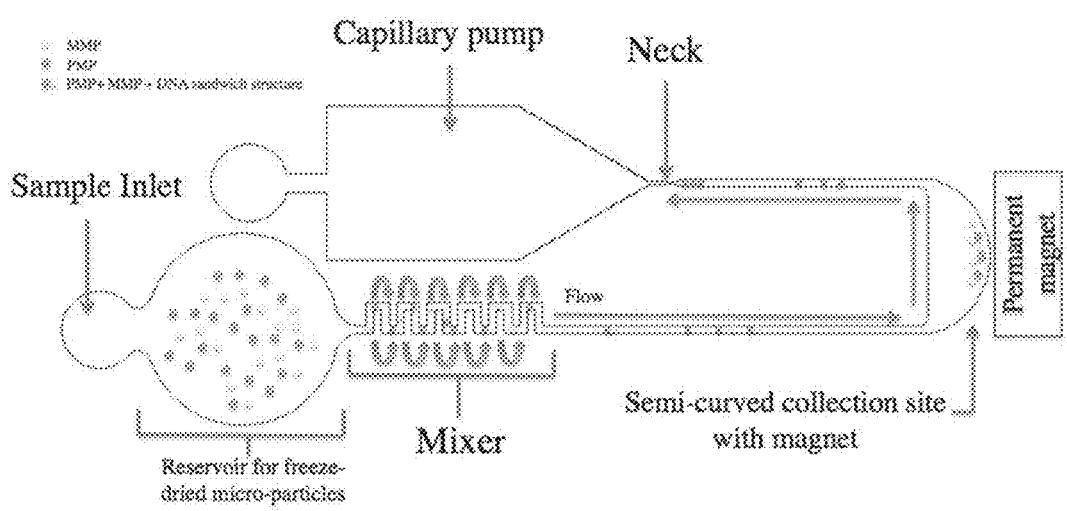
FIG. 21 shows a schematic diagram of a device suitable for determining the amount of polystyrene particles in complexes collected in the methods of the present invention.

AuNP amplification. To conduct detection without AuNP amplification, two types of oligonucleotide probes, M155 and Bi155, were used with sequences complementary to that of the target oligonucleotide MB155 in juxtaposition. M155 and Bi155 were loaded to MMPs and PMPs, respectively, and MMPs-targets-PMPs were formed after hybridization. The result showed that we can detect the concentration as low as 250 pM (FIG. 19; relative absorbance, 0.94, total volume for hybridization, 45 μL).

Compared to the detection with AuNP amplification, a similar readout was achieved for MB155 at 1 pM (FIG. 13; relative absorbance, 0.91, total volume for hybridization, 45 μL). Thus, the amplification rate is about 250.

Selectivity of Single-Nucleotide Polymorphisms

Figure 14A:
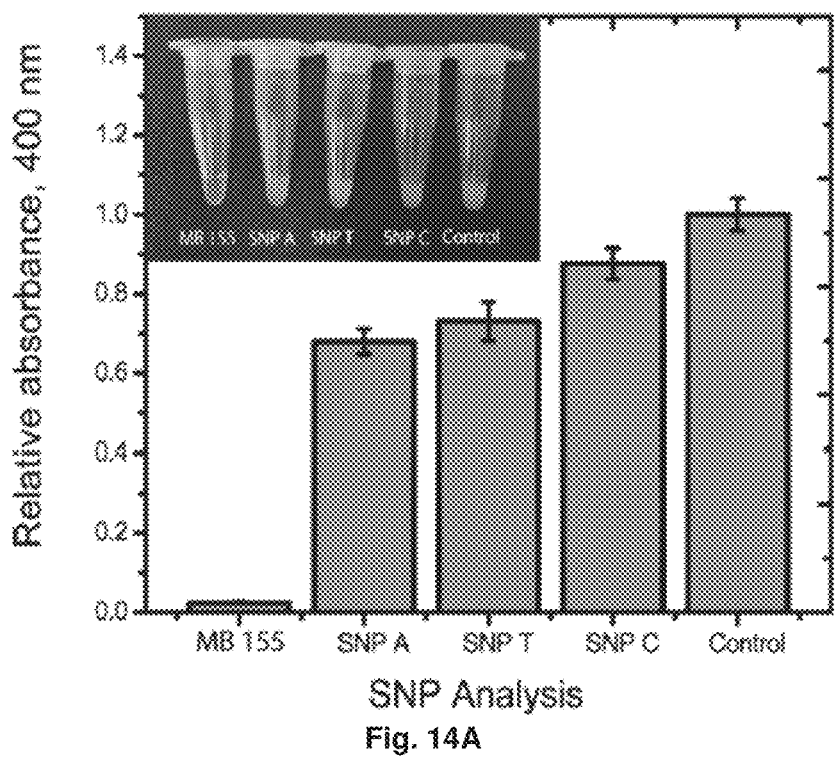
FIGS. 14A and 14B show the detection of target nucleic acid sequence with single-base-mismatched sequence at 250 pM in 45 μL.
Figure 14B:
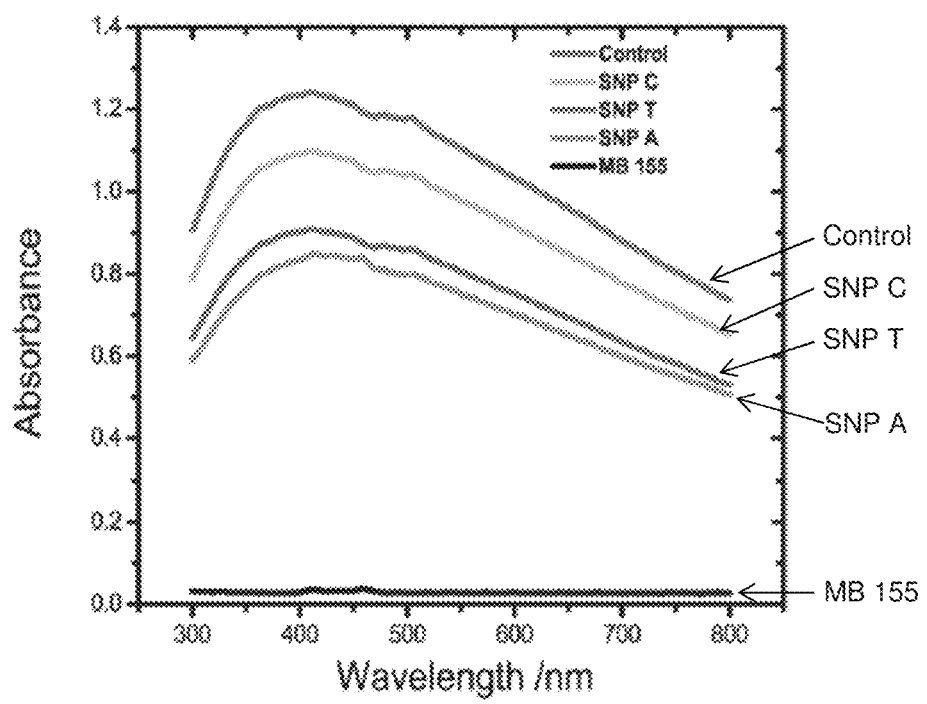

The selectivity of single-nucleotide polymorphisms, which is important for preventing non-specific bindings and applications in gene expression assays, was determined. The seventh base Gin MB155 was replaced by A, T, and C (SNP A, SNP T, and SNP C, respectively; Table 2). Using 250 pM in 45 μL, a concentration above the linear range, the results showed that although the solution turbidity become transparent for target molecules with complementary sequence the single-base mismatched sequence caused the solution to remain opaque (FIG. 14A). In addition, as measured by UV-VIS spectrometer, there was only a slight decrease of absorbance compared to that of the control sample (FIG. 14B). The selectivity contrast ratio of SNP A, SNP T, and SNP C is 28, 30, and 36, respectively. Therefore, this result demonstrates the selectivity of this method for differentiating between target oligonucleotides with single-base-mismatched sequences.

Detection Performed in a Serum Environment

The presence of nucleic acid sequence in complex biofluid such as blood serum, which contains many interfering materials, e.g., protein, RNAs, DNase/RNase, may create considerable challenges or even complete failure of detection. To demonstrate the compatibility with complex bio-fluid, the detection of target oligonucleotides MB155 with varying concentration in the blood serum was performed.

Figure 15A:
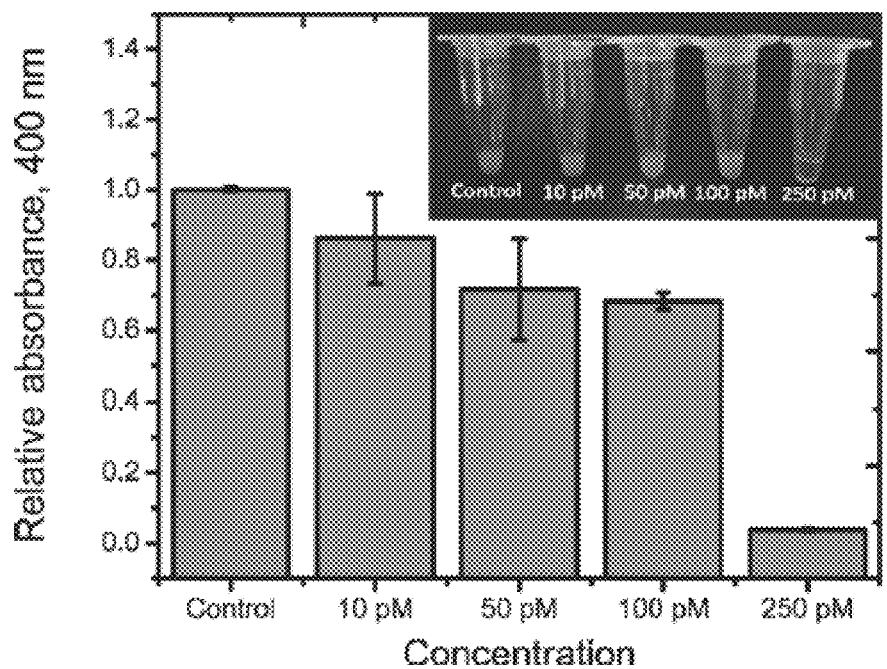
FIGS. 15A and 15B show the detection of target nucleic acid sequence MB155 in blood serum.
Figure 15B:
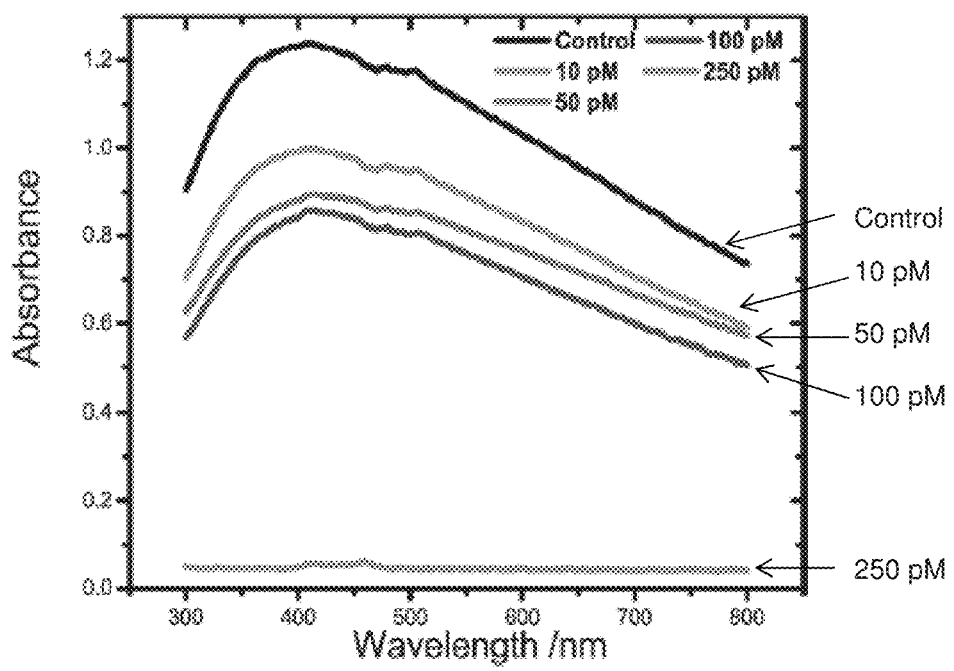

The results showed that the solution turbidity can still gradually changed from transparent to opaque with addition of target oligonucleotides (FIG. 15) where the LOD was 100 pM in 45 µL by naked eyes and 2.7 pM in 45 µL by UV-VIS spectra measurement (linear range, 0-100 pM, calculated on the basis of 3σ/m) demonstrating the compatibility with complex bio-fluid.

Detection of RNAs Extracted from Cells

MicroRNAs derived from in vitro cell culture were detected. The target oligonucleotide MB155 was designed with a sequence the same as a type of microRNA, miR-155, that is highly expressed in breast cancer cells (MDAMB-231). The oligonucleotide probes used above can be directly applied for detecting the miR-155 extracted from MDA-MB-231 cells. For comparison, the RNAs extracted from MCF-10A cells, the breast epithelial cell line was also used as a reference.

Figure 16A:
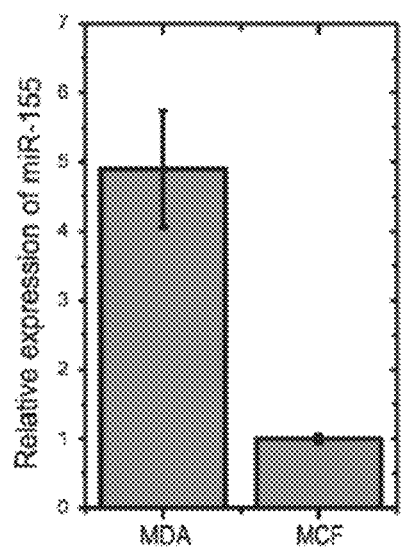
FIGS. 16A, 16B, 16C, 16D, 16E shows the detection of microRNA miR-155 extracted from MDA-MB-231 cells (MDA) or MCF-10A cells (MCF).
Figure 16B:
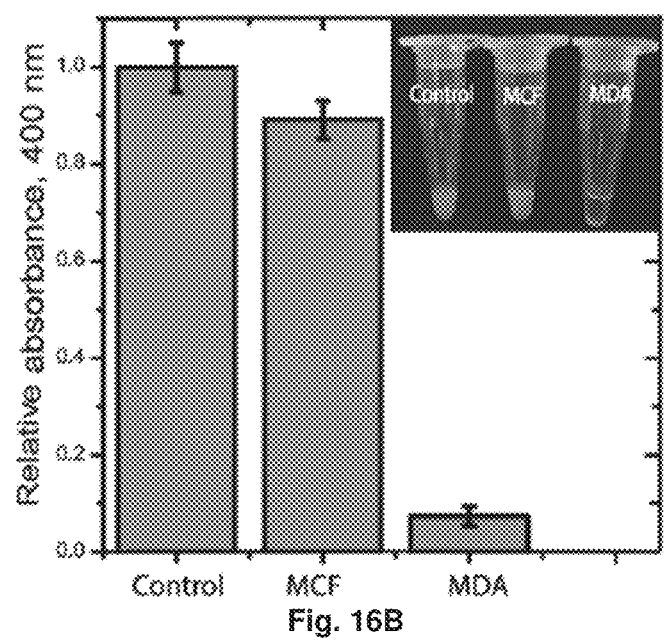
Figure 16C:
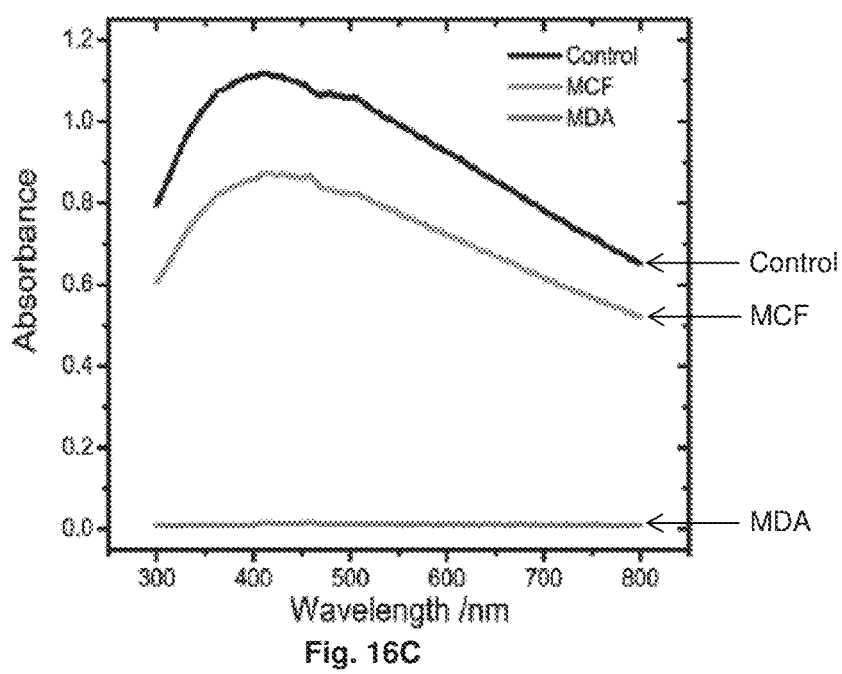

The expression level of miR-155 for both cell types was firstly investigated. Using qRT-PCR, the results showed that the miR-155 was indeed highly expressed in MDA-MB-231 cells but not in MCF-10A cells (FIG. 16A). After isolating the total RNAs from both cell types, the RNA solution was directly applied to the AuNP amplified assay. The results showed a significant decrease of absorbance for RNA samples from MDA-MB-231 cells, suggesting that miR-155 was detected (FIGS. 16B and 16C). In contrast, for the MCF-10A cells, there was only a slight decrease of absorbance compared to the control sample, which may have resulted from the nonspecific adsorption of cellular components or low expression of miR-155 in cell lysates.

Figure 16D:
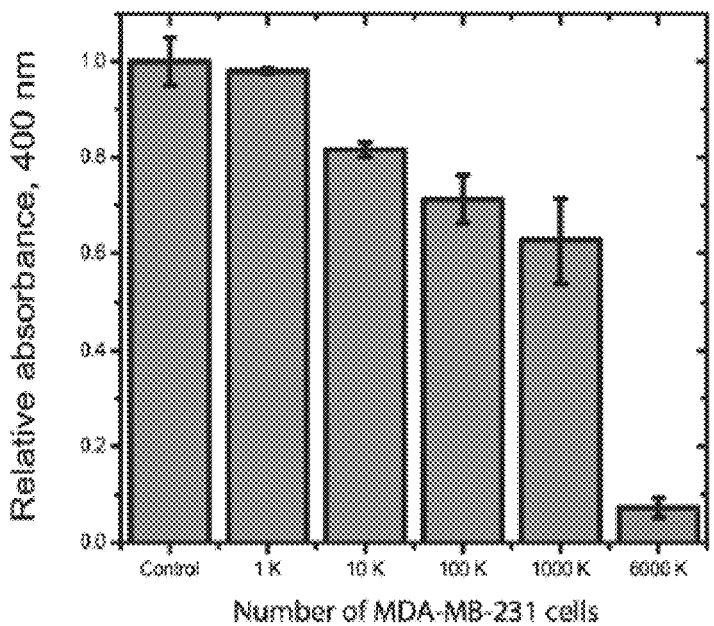

Furthermore, using different numbers of MDA-MB-231 cells for detection, the results showed a quantitative correlation between the absorbance and cell number, demonstrating the potential for quantitative analysis of our assays (FIG. 16D).

Figure 16E:
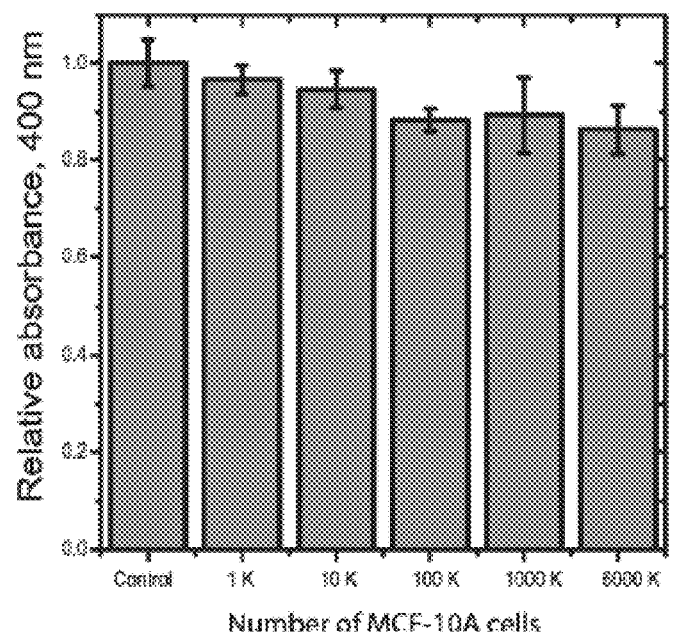

For MCF-10A cells, the decrease of absorbance remained at a similar level regardless of the increase of cell number (FIG. 16E). Consequently, the result indicates that the method of the present invention provides a potential solution for the detection of microRNAs and disease diagnosis with quantitative readouts.

The invention claimed is:

1. A method for determining a presence or amount of a target nucleic acid sequence in a sample comprising steps of:

(a) adding a magnetic particle loaded with a first probe and a polystyrene particle loaded with a second probe to the sample and applying conditions such that the target nucleic acid sequence in the sample binds to the loaded magnetic particle and to the loaded polystyrene particle to form a complex comprising the target nucleic acid sequence bound to the loaded magnetic particle and to the loaded polystyrene particle;

(b) applying a magnetic force to separate the complex from the mixture of step (a);

(c) determining at least one of a physical feature of the mixture after separating the complex in step (b) or the amount of the complex separated in step (b);
wherein step (c) further comprises steps of:

(i) isolating the complex separated in step (b), optionally purifying the complex and suspending it in a mixture;

(ii) introducing the mixture after step (i) to a device having an inlet port and a micro-channel, wherein the micro-channel comprises a neck portion with a diameter smaller than the size of the loaded polystyrene particle;

(iii) determining the amount of the polystyrene particle from the complex being trapped in the micro-channel, and optionally comparing the determined amount with a reference value wherein the method further comprises a step of loading the magnetic particle with the first probe and loading the polystyrene particle with the second probe prior to step (a) and wherein a blocker nucleic acid sequence having a region at least partially complementary to the first probe and another region at least partially complementary to the second probe is additionally loaded to each of the magnetic particle and the polystyrene particle.

2. The method according to claim 1, wherein the first probe and second probe are single strand nucleic acid sequences linked to biotin.

3. The method according to claim 1, wherein step (a) comprises steps of:
   (i) adding the loaded magnetic particle to the sample and applying conditions such that the target nucleic acid sequence in the sample binds to the loaded magnetic particle;
   (ii) separating the loaded magnetic particle optionally bound to the target nucleic acid sequence from the mixture of step (i) by applying a magnetic force;
   (iii) adding a mixture containing the loaded polystyrene particle to the separated loaded magnetic particle separated in step (ii), and applying conditions such that the target nucleic acid sequence in the bound loaded magnetic particle binds to the loaded polystyrene particle to form the complex.

4. The method according to claim 1, wherein the physical feature in step (c) is at least one of the colour, turbidity or spectral absorbance of the mixture and it is determined by UV-Vis spectrometry.

5. The method according to claim 1, wherein the micro-channel is marked with one or more indicia.

6. A method for determining a presence or amount of a target nucleic acid sequence in a sample comprising steps of:
   (a) adding a first magnetic particle loaded with a first probe and a gold particle loaded with a second probe to the sample and applying conditions such that the target nucleic acid sequence in the sample binds to the first loaded magnetic particle and to the loaded gold particle to form a first complex comprising the target nucleic acid sequence bound to the first loaded magnetic particle and to the loaded gold particle;
   (b) applying a magnetic force to separate the first complex from the mixture of step (a);
   (c) separating the loaded gold particle from the first complex separated in step (b);
   (d) adding a second magnetic particle loaded with a third probe and a polystyrene particle loaded with a fourth probe to the loaded gold particle of step (c) and applying conditions such that the second probe of the loaded gold particle binds to the second loaded magnetic particle and to the loaded polystyrene particle to form a second complex comprising the second probe of the loaded gold particle bound to the second loaded magnetic particle and to the loaded polystyrene particle; and
   (e) applying a magnetic force to separate the second complex from the mixture of step (d);
   (f) determining at least one of a physical feature of the mixture after separating the second complex in step (e) or the amount of the second complex separated in step (e);
   wherein step (f) further comprises steps of:
   (i) isolating the separated second complex, optionally purifying the second complex and suspending it in a mixture;
   (ii) introducing the mixture after step (i) to a device having an inlet port and a micro-channel, wherein the micro-channel comprises a neck portion with a diameter smaller than the size of the loaded polystyrene particle;
   (iii) determining the amount of the loaded polystyrene particle from the second complex being trapped in the micro-channel, and comparing the determined amount with a reference value;
   wherein the second loaded magnetic particle and the loaded polystyrene particle are additionally loaded with a blocker nucleic acid sequence having a region at least partially complementary to the third probe and another region at least partially complementary to the fourth probe.

7. The method according to claim 6, wherein the first, third and fourth probes are single strand nucleic acid sequences linked to biotin, and the second probe is a single strand nucleic acid sequence linked to a thiol group.

8. The method according to claim 6, wherein step (a) comprises steps of:
   (i) adding the first loaded magnetic particle to the sample and applying conditions such that the target nucleic acid sequence in the sample binds to the first loaded magnetic particle;
   (ii) separating the first loaded magnetic particle optionally bound to the target nucleic acid sequence from the mixture of step (i) by applying a magnetic force;
   (iii) adding a mixture containing the loaded gold particle to the separated first loaded magnetic particle, and applying conditions such that the target nucleic acid sequence in the bound first loaded magnetic particle binds to the loaded gold particle to form the complex.

9. The method according to claim 6, wherein in step (c), the loaded gold particle is separated from the first complex by heating.

10. The method according to claim 6, wherein the physical feature in step (f) is at least one of the colour, turbidity or spectral absorbance of the mixture.

11. The method according to claim 6, wherein the micro-channel is marked with one or more indicia.

* * * * *

SEQUENCE LISTING

<160> NUMBER OF SEQ ID NOS: 22

<210> SEQ ID NO 1
<211> LENGTH: 30
<212> TYPE: DNA
<213> ORGANISM: Artificial Sequence
<220> FEATURE:
<223> OTHER INFORMATION: Single nucleic acid sequence

<400> SEQUENCE: 1
acttgtgtct cgtttcttcg atccaaagcg                                    30

<210> SEQ ID NO 2
<211> LENGTH: 15
<212> TYPE: DNA
<213> ORGANISM: Artificial Sequence
<220> FEATURE:
<223> OTHER INFORMATION: Single nucleic acid sequence

<400> SEQUENCE: 2
aaacgagaca caagt                                                    15

<210> SEQ ID NO 3
<211> LENGTH: 15
<212> TYPE: DNA
<213> ORGANISM: Artificial Sequence
<220> FEATURE:
<223> OTHER INFORMATION: Single nucleic acid sequence

<400> SEQUENCE: 3
cgctttggat cgaag                                                    15

<210> SEQ ID NO 4
<211> LENGTH: 15
<212> TYPE: DNA
<213> ORGANISM: Artificial Sequence
<220> FEATURE:
<223> OTHER INFORMATION: Single nucleic acid sequence

<400> SEQUENCE: 4
ctcgaactgg agtga                                                    15

```
<210> SEQ ID NO 5
<211> LENGTH: 30
<212> TYPE: DNA
<213> ORGANISM: Artificial Sequence
<220> FEATURE:
<223> OTHER INFORMATION: Single nucleic acid sequence

<400> SEQUENCE: 5
atgccatttg agattttga attccgtggt                                    30

<210> SEQ ID NO 6
<211> LENGTH: 15
<212> TYPE: DNA
<213> ORGANISM: Artificial Sequence
<220> FEATURE:
<223> OTHER INFORMATION: Single nucleic acid sequence

<400> SEQUENCE: 6
aatctcaaat ggcat                                                   15

<210> SEQ ID NO 7
<211> LENGTH: 15
<212> TYPE: DNA
<213> ORGANISM: Artificial Sequence
<220> FEATURE:
<223> OTHER INFORMATION: Single nucleic acid sequence

<400> SEQUENCE: 7
accacggaat tcaaa                                                   15

<210> SEQ ID NO 8
<211> LENGTH: 30
<212> TYPE: DNA
<213> ORGANISM: Artificial Sequence
<220> FEATURE:
<223> OTHER INFORMATION: Single nucleic acid sequence

<400> SEQUENCE: 8
acttgtgact cgtttcttcg atccaaagcg                                   30

<210> SEQ ID NO 9
<211> LENGTH: 30
<212> TYPE: DNA
<213> ORGANISM: Artificial Sequence
<220> FEATURE:
<223> OTHER INFORMATION: Single nucleic acid sequence

<400> SEQUENCE: 9
acttgtggct cgtttcttcg atccaaagcg                                   30

<210> SEQ ID NO 10
<211> LENGTH: 30
<212> TYPE: DNA
<213> ORGANISM: Artificial Sequence
<220> FEATURE:
<223> OTHER INFORMATION: Single nucleic acid sequence

<400> SEQUENCE: 10
acttgtgcct cgtttcttcg atccaaagcg                                   30

<210> SEQ ID NO 11
<211> LENGTH: 60
<212> TYPE: DNA
<213> ORGANISM: Artificial Sequence
<220> FEATURE:
```

<223> OTHER INFORMATION: Single nucleic acid sequence

<400> SEQUENCE: 11
acttgtgtct cgtttaaaaa aaaaaaaaaa aaaaaaaaaa aaaaacttcg atccaaagcg    60

<210> SEQ ID NO 12
<211> LENGTH: 90
<212> TYPE: DNA
<213> ORGANISM: Artificial Sequence
<220> FEATURE:
<223> OTHER INFORMATION: Single nucleic acid sequence

<400> SEQUENCE: 12
acttgtgtct cgtttaaaaa aaaaaaaaaa aaaaaaaaaa aaaaaaaaaa aaaaaaaaaa    60
aaaaaaaaaa aaaaacttcg atccaaagcg                                    90

<210> SEQ ID NO 13
<211> LENGTH: 11
<212> TYPE: DNA
<213> ORGANISM: Artificial Sequence
<220> FEATURE:
<223> OTHER INFORMATION: Single nucleic acid sequence

<400> SEQUENCE: 13
cccctatcac g                                                        11

<210> SEQ ID NO 14
<211> LENGTH: 25
<212> TYPE: DNA
<213> ORGANISM: Artificial Sequence
<220> FEATURE:
<223> OTHER INFORMATION: Single nucleic acid sequence

<400> SEQUENCE: 14
attagcatta aactcggatc actcg                                         25

<210> SEQ ID NO 15
<211> LENGTH: 11
<212> TYPE: DNA
<213> ORGANISM: Artificial Sequence
<220> FEATURE:
<223> OTHER INFORMATION: Single nucleic acid sequence

<400> SEQUENCE: 15
attagcatta a                                                        11

<210> SEQ ID NO 16
<211> LENGTH: 22
<212> TYPE: DNA
<213> ORGANISM: Artificial Sequence
<220> FEATURE:
<223> OTHER INFORMATION: Single nucleic acid sequence

<400> SEQUENCE: 16
ttaatgctaa tcgtgatagg gg                                            22

<210> SEQ ID NO 17
<211> LENGTH: 22
<212> TYPE: RNA
<213> ORGANISM: Artificial Sequence
<220> FEATURE:
<223> OTHER INFORMATION: Single nucleic acid sequence

<400> SEQUENCE: 17
uuaaugcuaa ucgugauagg gg                                            22

```
<210> SEQ ID NO 18
<211> LENGTH: 22
<212> TYPE: DNA
<213> ORGANISM: Artificial Sequence
<220> FEATURE:
<223> OTHER INFORMATION: Single nucleic acid sequence

<400> SEQUENCE: 18
ttaatactaa tcgtgatagg gg                                              22

<210> SEQ ID NO 19
<211> LENGTH: 22
<212> TYPE: DNA
<213> ORGANISM: Artificial Sequence
<220> FEATURE:
<223> OTHER INFORMATION: Single nucleic acid sequence

<400> SEQUENCE: 19
ttaattctaa tcgtgatagg gg                                              22

<210> SEQ ID NO 20
<211> LENGTH: 22
<212> TYPE: DNA
<213> ORGANISM: Artificial Sequence
<220> FEATURE:
<223> OTHER INFORMATION: Single nucleic acid sequence

<400> SEQUENCE: 20
ttaatcctaa tcgtgatagg gg                                              22

<210> SEQ ID NO 21
<211> LENGTH: 13
<212> TYPE: DNA
<213> ORGANISM: Artificial Sequence
<220> FEATURE:
<223> OTHER INFORMATION: Single nucleic acid sequence

<400> SEQUENCE: 21
gtttaatgct aat                                                        13

<210> SEQ ID NO 22
<211> LENGTH: 12
<212> TYPE: DNA
<213> ORGANISM: Artificial Sequence
<220> FEATURE:
<223> OTHER INFORMATION: Single nucleic acid sequence

<400> SEQUENCE: 22
cgagtgatcc ga                                                         12
```